United States Patent
Ranu

(10) Patent No.: US 6,723,839 B1
(45) Date of Patent: Apr. 20, 2004

(54) PARTIAL GENE SEQUENCE FROM PELARGONIUM TO CONTROL ETHYLENE LEVELS IN GERANIUMS

(75) Inventor: Rajinder S. Ranu, Fort Collins, CO (US)

(73) Assignee: Colorado State University through its agent Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 09/975,842

(22) Filed: Oct. 12, 2001

Related U.S. Application Data

(63) Continuation-in-part of application No. 09/776,529, filed on Feb. 2, 2001, which is a continuation of application No. 09/171,482, filed as application No. PCT/US97/17644 on Sep. 30, 1997, now Pat. No. 6,184,449, which is a continuation-in-part of application No. 08/724,194, filed on Oct. 1, 1996, now Pat. No. 5,824,875.
(60) Provisional application No. 60/239,782, filed on Oct. 12, 2000.

(51) Int. Cl.[7] .......................... C12N 15/11; C12N 15/29
(52) U.S. Cl. ...................... 536/23.6; 536/23.2; 536/23.1
(58) Field of Search ............................... 536/23.1, 23.2, 536/23.6; 435/183, 320.1

(56) References Cited

U.S. PATENT DOCUMENTS

| | | | |
|---|---|---|---|
| 4,237,224 A | 12/1980 | Cohen et al. | 435/68 |
| 4,468,464 A | 8/1984 | Cohen et al. | 435/317 |
| 4,740,463 A | 4/1988 | Weinberg et al. | 435/172.3 |
| 4,740,470 A | 4/1988 | Cohen et al. | 435/172.3 |
| 4,782,022 A | 11/1988 | Puhler et al. | 435/172.3 |
| 4,801,540 A | 1/1989 | Hiatt et al. | 435/172.3 |
| 4,962,028 A | 10/1990 | Bedbrook et al. | 435/172.3 |
| 5,107,065 A | 4/1992 | Shewmaker et al. | 800/205 |
| 5,123,951 A | 6/1992 | See et al. | 71/86 |
| 5,208,149 A | 5/1993 | Inouye | 435/91 |
| 5,272,065 A | 12/1993 | Inouye et al. | 435/91.1 |
| 5,378,619 A | 1/1995 | Rogers | 435/172.3 |
| 5,416,250 A | 5/1995 | Ferro et al. | 800/205 |
| 5,565,347 A | 10/1996 | Fillatti et al. | 435/172.3 |
| 5,674,731 A | 10/1997 | Lin et al. | 435/240.4 |
| 5,689,055 A | 11/1997 | Meyerowitz et al. | 800/205 |
| 5,723,766 A | 3/1998 | Theologis et al. | 800/205 |
| 5,759,829 A | 6/1998 | Shewmaker et al. | 435/172.3 |
| 5,824,868 A | 10/1998 | Meyerowitz et al. | 800/205 |
| 5,824,875 A | 10/1998 | Ranu | 800/205 |
| 5,929,302 A | 7/1999 | Kellogg et al. | 800/278 |
| 5,955,652 A | 9/1999 | Ecker et al. | 800/298 |
| 5,965,987 A | 10/1999 | Murata et al. | 315/85 |
| 5,981,727 A | 11/1999 | Baden et al. | 536/23.6 |
| 5,998,702 A | 12/1999 | Boeshore et al. | 800/306 |

FOREIGN PATENT DOCUMENTS

| | | | | |
|---|---|---|---|---|
| WO | WO 96/21027 | * | 7/1996 | A01H/5/00 |
| WO | WO 97/17429 | | 5/1997 | |

OTHER PUBLICATIONS

Fourgoux–Nicol et al., 1999, Plant Molecular Biology, vol. 40; pp. 857–872.*
Broun P. et al. Science vol. 282; Nov. 13, 1998, pp. 1315–1317.*
Accession AAT33136.*
Accession AAT33139.*
Welch J. et al. Nucleic Acids Research, Dec. 25, 1990; vol. 18, No. 24; pp. 7213–7218.*
Abel, S., et al, "ASC4, a Primary Indoleacetic Acid–responsive Gene Encoding 1–Aminocyclopropane–1–carboxylate Synthase in *Arabidopsis thaliana*", vol. 270, 32:19093–19099 (1995).
Abeles, et al, "Genes Involved in Ethylene Biogenesis", Ethylene In Plant Biology, 2nd Ed., (1992), pp. 251–252.
Abeles, et al, "The Biosynthesis of Ethylene", Ethylene In Plant Biology, 2nd Ed, (1992), pp. 26–55.
Abeles, F.B., et al., Ethylene in Plant Biology., (1992), pp. 285–291 and 1–13.
Adams, D.O., et al., "Ethylene biosynthesis: Identification of 1–aminocyclopropane–1–carboxylic acid as an intermediate in the conversion of methonine to ethylene", Proc. Nat'l Acad Sci USA 76, 1979, pp. 170–174.
Alberts, B., et al., Molecular Biology of the Cell, 2nd Ed., Garland Publishing, Inc., New York, NY (1989), pp. 195–196.
Altschul, S.F., "Sequence Comparison and Alignment in DNA and Protein Sequence Analysis", (1989), pp. 137–167.
Altschul, S.F., et al, "Gapped Blast and PSI–BLAST: A New Generation Of Protein Database Search Programs", Nucleic Acids Research, (1997), pp. 3389–3402.
Amrhein, N., et al., "Identification of a Major Metabolite of the Ethylene Precursor 1–Aminocyclopropane–1–carboxylic Acid in Higher Plants.", Naturwissenschaften 68: 619–620 (1981).
An, et al., "Organ Specific and Developemental Regulation of the Nopaline Synthase Promoter in Transgenic Tobacco Plants.", Plant Physiology 88:547–552 (1988).
Apel, et al., "The Plastid Membranes of Barley (*Hordeum Vulgare*)", Eur. J. Became. 85:581–588 (1978).
Belagaje, R., et al., "Total Synthesis of a Tyrosine Suppressor Transfer RNA Gene", J. Biol. Chem. 254:5765–5780 (1979).

(List continued on next page.)

*Primary Examiner*—David T. Fox
*Assistant Examiner*—Russell Kallis
(74) *Attorney, Agent, or Firm*—Santangelo Law Offices, P.C.

(57) ABSTRACT

A novel ACC synthase gene in geranium PHSacc-25. PHSacc-25 was identified by amplifying isolated mRNA using polymerase chain reaction, the resulting cDNAs were cloned into a plasmid, positive clones were isolated, and the cDNA insert was partially sequenced. A portion of the DNA sequence encoding for the enzyme ACC synthase in geranium plants (specifically from *Pelargonium hortorum* cv Sincerity) was identified. The cDNA sequence corresponds to a gene which may be important in the control of ethylene production.

1 Claim, 3 Drawing Sheets

OTHER PUBLICATIONS

Benfey, et al., "The Camv 35s Enhancer Contains Atleast Two Domains Which Can Confer Different Developemental and Tissue Specific Expression Patterns" EMBO J. 8: 2195–2202 (1989).

Bevan, et al., Tissue and Cell specific activity of a phenylaline ammonia–lylase prmoter EMBO J. 8:1899–1906 (1989).

Binding, H., "Regeneration of Plants", Plant Protoplasts, pp. 21–73, (1985).

Boehinger–Mannheim, "The Genius System Users Guide for Filter Hybridization", Version 2.0, 1992, pp. 6–100.

Botella, J.R., et al, "Identification and Characterization of a Full–length Cdna Encoding for an Auxin–induced 1–aminocyclopropane–1–carboxylate Synthase from Etiolated Mung Bean Hypocotyl Segments and Expression of its Mrna in Reponse to Indole–3–acetic Acid", Plant Molecular Biol 20, pp. 425–436 (1992).

Botella, J.R., et al., "Identification and characterization of three putative genes for 1–Aminocyclopropane–1–carboxylate Synthase from etiolated mung bean hypocotyl segments", Plant Mol Biol 18, pp. 793–797 (1992).

Botella, J.R., et al, "Identification of two new members of the 1–Aminocyclopropane–1–carboxylate Synthase–Encoding Multigene family in mung bean", Gene 06852, pp. 249–253, (1993).

Brach, M.A., "The Mitogenic Response to Tumor Necrosis Factor Alpha Requires C–Jun/AP–1", Molec. Cell. Biol. vol. 13, No. 7, pp. 4284–4290 (1993).

Breathnanch, R. and Chambon, P., "Organization and Expression of Eucaryotic Split Genes Coding for Proteins", Biochem Annual Review, (1981), vol. 50, pp. 349–383.

Chomczynski, P., et al., "Single–step method of RNA Isolation by Acid Guanidinium Thiocyanate–Phenol–Chloroform Extraction", Analytical Biochemistry, vol. 162, pp. 156–159 (1987).

Coruzzi, et al., "Tissue Specific and Light Regulated Expression of a pea nuclear gene encoding the small subunit of ribulose–1,5–bisphosphate carboxylate", EMBO Journal, vol. 5, No. 8, pp. 1671–1679 (1984).

Dale, P.J., "Protoplast Culture and Plant Regeneration of Cereals and Other Recalcitrant Crops", Protoplasts, pp. 31–41, (1983).

Davey, M.R., "Recent Developments in the culture and Regeneration of Plant Protoplasts", Protoplasts, pp. 12–29, (1983).

De La Pena, et al., Transgenic Rye Plants Obtained by Injecting DNA into young Floral Tillers, Letters to Nature, Nature, vol. 325, pp. 274–276, (1987).

Deikman, J. and Fischer R., L. "Interaction of a Dna Binding Factor with 5'flanking Regioin of an Ethylene–responsive Fruit Ripening Gene from Tomato", The EMBO, Journal 7, pp. 3315–3320 (1998).

Ditta, G., et al., "Broad Host Range DNA Cloning System for Gram Negative Bacteria: Construction of a Gene Bank of Rhizobium Meliloti", Proc. Natl. Acad. Science, vol. 77, No. 12, 7347–7451 (1980).

Dong, J.G., et al, "Cloning of a Cdna Encoding 1–aminocyclopropane–1–carboxylate Synthase and Expression of its Mrna in Ripening Apple Fruit", Planta, pp. 38–45 (1991).

Evans, D.A., and Bravo, J.E., "Protoplast Isolation and Culture", Handbook of Plant Cell Cultures, 124–176 (1983).

Fan, D. et al, "Cloning and Characterization of the Cdna Encoding 1–aminocyclopropane–1–carboxylate(Acc) Synthase from Pelargonium Hortorum–sincerity", CSU, The FASEB Journal, vol. 2368, pp. 1410 (1986).

Fan, J.G., Smith, C., Ranu, R.S., and Fuller, C.W. "Dna Sequencing with [a–33p] Labeled Ddntp Terminators: a New Approach to Dna Sequencing with Thermo Sequnase Dna Polymerase", CSU, Biotechniques, pp. 1132–1137 (1996).

Firoozabady, E., et al, "Regeneration of transgenic rose (Rosa hybrida) plants from embryogenic tissue", Bio/Technol., vol. 12, Jun. 1994, pp. 609–613.

Frischauf, A.M., Leharch, H., Poustka, A., and Murray, N. "Lambda Replacement Vectors Carrying Polylinker Dequences", J. Molecular Biology, vol. 170, pp. 827–842 (1983).

Fromm, M., et al., Proc. Natl. Acad. Sci. USA 82:5824 (1985).

Fry, et al., "Transformation of Brassica Napus with Agrobacterium tumefaciens based vectors", Plant Cell Reports, vol. 6, pp. 321–325 (1987).

Gautier, et al., "a–DNA IV: a–anomeric tetrathymidylates covately linked to intercalating oxazolopyridocarbazole. Synthesis, physiochemical properties and poly (Ra) binding", Nucl. Acids Res., vol. 15, pp. 6625–6641 (1987).

GenBank User Services, "Release Date of U17229", E–mail message, Apr. 22, 1998.

Graves, et al., "The transformation of Zea Mays seedlings with agrobacterium tumefaciens", Plant Mol. Biol. vol. 7, pp. 43–50 (1986).

Gray, J.E., et al, "Altered Gene Expression, Leaf Senescence, and Fruit Ripening by Inhibiting Ethylene Synthesis with EFE–Antisense Genes", Cellular and Molecular Aspects of the Plant Hormone Ethylene, pp. 82–89, (1993).

Grimsley, et al., "Agrobacterium mediated delivery of infectious maize streak virus into maize plants", Nature, vol. 325, pp. 177–179 (1987).

Grimsley, et al., "Meristemic tissues of maize plants are most susceptible to agroinfectio with maize streak virus", Bio–Technology vol. 6, 185–190, (1988).

Guillemaut, P. and Marechal–Drouard, L. "Isolation of Plant Dna: A Fast, Inexpensive and Reliable Method", Plant Molecular Biology Reporter, vol. 10, pp. 60–65 (1992).

Guilley, H., et al., "Transcription of califlower mosaic virus DNA: Detection of Promoter Sequences, and Chracterization of Transcripts", Cell, vol. 30, pp. 763–773 (1982).

Guiltinan, M.J., Marcotte, W.R., and Quatrano, R.S. "A Plant Leucine Ziper Protein That Recognizes an Abscisic Acid Response Element", Science, vol. 10, pp. 267–271 (1990).

Gurley, et al., "Upstream Sequences Required for Efficient Expression of a Soybean Heat Shock Gene.", Mol. Cell Biol. vol. 6 pp. 559–565 (1986).

Ha, et al., "Cis–scting regulatory elements controlling temporal and organ specific activity of nopaline synthase promoter", Nucl. Acids Res., vol. 17, pp. 215–224, (1989).

Hames, B.D., et al., Nucleic Acid Hybridisation: A Practical Approach, IRL Press, Washington, DC pp. 1–13, (1985).

Hamilton, AJ, et a, "Antisense Gene that Inhibits Synthesis of the Hormone Ethylene in Transgenic Plants", Nature, pp. 284–287, (1990).

Henskens, D., et al, "Expression of Two ACC Synthase mRNAs In Carnation Flower Parts During Aging and Following Treatment With Ethylene", Agrotechnological Research Institute, pp. 323–324, (1993).

Herrera–Estrella, et al., "Light inducible and chloroplast associated expression of a chinaeric gene introduced into Nicotiana Tabacum using a TI plasmid vector", Nature, vol. 310, pp. 115–120, (1984).

Hoffman, N.E., et al., "Identification of a 1–(malonylamino)cyclopropane 1–carboxylic acid as a major conjugate of 1–aminocyclopropane–1–carboxylic acid, an athylene precursor in Higher Plants", (1982), Biochem Biophys. Res. Commun. vol. 104, No. 2, pp. 765–770.

Hooykaas–Van Slogteren, et al., "Expression of TI plasmid genes in monocotyledonous plants infected with agrobacterium tumefaciens", Nature, vol. 311, pp. 763–764 (1984).

Horsch, et al., "A Simple and General Method for Tranferring Genes into Plants", Science, vol. 227, pp. 1229–1231, (1985).

Huang, P.L., Park J.E., and Rottmann, W.H., "Theologis: a Two Genes Encoding I–Aminocyclopropane–i–Carboxylate Synthase in Zucchini (Cucurbita Pepo) Are Clustered and Similar but Differentially Regulated", Proc Nad Acad Sci, (1991), pp. 7021–7025.

Hull, et al., "The Sequence of carnation etched ring virus DNA: comparison with cauliflower masaic virus and retroviruses", The EMBO Jornal, vol. 5 No. 12, pp. 3083–3090 (1986).

Jefferson, et al., "GUS Fusions: B–glucuronidase as a sensitive and versitile gene fusion marker in higher plants", EMBO J. 6:3901–3907 (1987).

Jensen, J.S., et al., "Nodule–specific expression of a chimaeric soybean leghaemoglobin gene in transgenic Lotus Corniculatus", Nature 321:669–674 (1986).

John, M.E., "An efficient method for isolation of RNA and DNA from plants containing polyphenolics", Nucleic Acids Research (1992), pp. 2381.

Jones, et al., "High Level Expression of introduced chiamaeric genes in regenerated transformed plants", (1985), The EMBO Journal, vol. 4, pp. 2411–2418.

Karlin, S. and Altschul, S., "Methods For Assessing The Statistical Significance Of Molecular Sequence Features By Using General Scoring Schemes", Proc. Natl. Acad. Sci., (1990), pp. 2264–2268.

Karlin, S. and Altschul, S., "Applications and Statistics For Multiple High–Scoring Segments In Molecular Sequences", Proc. Natl. Acad. Sci., (1993), pp. 5873–5877.

Kay, et al., "Duplication of Camv 35s Promoter Sequences Creates a Strong Enhancer for Plant Genes" Science 236:1299–1302 (1987).

Kende, H., et al, "Ethylene Biosynthesis: Annual Review of Plant Physiology", Plant Molecular Biology, (1993), pp. 283–307.

Kende, H., Hoffmann–Benning, S. and Sauter, M. "The Role of Ethylene in Regulating Growth of Deepwater Rice," MSU Plant Research Laboratory, (1993), pp. 329–334.

Khorana, H.G., "Total Synthesis of a Gene", Science, vol. 203, pp. 614–625 (1979).

Kim, W.T., et al., "Induction of 1–aminocyclopropane–1–carboxylate Synthase MRNA by Auxin in Mung Bean Hypocotyls and Cultured Apple Shoots", (1991), Plant Physiol 98:465–471.

Kionka, C., et al, "The Enzymatic Malonylation of 1–aminocyclopropane–1–carboxylic Acid in Homogenates of mung bean hypocotyls", Planta 162: 226–235, (1984).

Klee, et al., "Control of Ethylene Synthesis by Expression of a becterial enzyme in Trangenic Tomato plants.", (1991), Plant Cell 3: 1187–1193.

Klein, et al., "Factors Influencing Gene Delivery in ZEA may Cells by High Velocity Micro Projectiles", Bio/Technology 6:559–563 (1988).

Köck, M., et al., "A Gene Involved in Ethylene Synthesis in a Tomato", (1991), Plant Mol Biol. 17:141–142.

Kretz, P. L., and Short, J. M., "Strategies of Molecular Biology", Mol. Biol. 2, (1989), pp. 25–26.

Kretz, P.L., Kohler, S. W., and Short, J. M. "Identification and Characterization of a Gene Responsible for Inhibiting Propogation at Methylated Dna Sequences in Mcra Mcrb I Escherichia Coli Strains", J. Bacteriol (1991), vol. 173, pp. 4707–4716.

Kretz, P.L., Reid, C.H., Greener, A., and Short, J. M., "Effect of Lambda Packaging Extract Mcr Restriction Activity on DNA Cloning", Nucleic Acids Res., (1989), vol. 17, pp. 5409.

Krol, et al., "Modulation of Eukaryotic Gene Expression by Complementary RNA and DNA sequences", Bio/Techniques, vol. 6, pp. 958–976, (1988).

Lambda Dash, "IIIBauHI Vector Kit", Stratagene Instructional Manual (1997), pp. 1–15.

Landsmann, et al., "Organ regulated Expression of the Parasponia andersonii haemoglobin gene in Transgenic tobacco Plants", Mol. Gene. Genet. vol. 214, pp. 68–73 (1988).

Lee J.S., "Alternative Dideoxy Sequencing of Double–Stranded Dna Cyclic Reaction Using Taq Polymerase", DNA Cell Biol. (1991), pp. 67–73.

Liang, X., et al, "The 1–aminocyclopropane–1–carboxylate synthase gene family of Arabidopsis thaliana", Proceedings of the National Academy of Sciences, (1992), pp. 11046–11050.

Lincoln, J.E. and Fischer, R.L. "Diverse Mechanisms for the Regulation of Ethylene Inducible Gene Expression", Molecular and General Genetics, (1993), pp. 71–75.

Lincoln, J.E., Campbell, A.D., Octiker, J., Rottomann, W.H., Oeller, P.W., and Shen, N.F., "Theologis: A Le–acs4, a Fruit Ripening and Wound–induced 1–Aminocyclopropane–i–Carboxylate Synthase Gene of Tomato (Lycopersicon Esculentum)", J. Biol. Chem, (1993), pp. 19422–19430.

Logemann, J., et al, "Improved Method for the Isolation of RNA from Plant Tissues", Anaytical Biochem (1987), pp. 16–20.

Lorz, et al., "Gene Transfer to Cereal Cells Mediated by Protoplast Transformation", Mol & Gen. Genet. vol. 199, pp. 178–182 (1985).

Maniatis, T., et al., "In Vitro Synthesis and Molecular Cloning of EuKarotic Structural Genes", Molecular Mechanisms in the Control of Gene Expression, Cold Spring Harbor Laboratory Press, Nierlich, D.P. et al, Acad Press, NY, vol. 5, pp. 513–533 (1976).

Manning, K., "Isolation of Nucleic Acids from Plants by Differential Solvent Precipitation", Analytical Biochemistry (1991), pp. 45–50.

Marton, L., "Transformation of Tobacco Cells By Coculture with Agrobacterium tumefaciens", Cell Culture and Somatic Cell Genetic of Plants 1: 514–521 (1984).

Michael, M.Z., et al, "Cloning of Ethylene Biosynthetic Genes Involved in Petal Senescence of Carnation and Petunia, and their Antisense Expression in Transgenic Plants", Cellular and Molecular Aspects of the Plant Hormone: Ethylene, (1993), pp. 298–303.

Miller, P.S., et al., "Biochemical and Biological effects of Nonianic Nucleic Acid Methylphosphonates", Biochemistry 20:1874–1880 (1981).

Morgan, M.E., and Saltveit, J.R. "Aging and Senescense", Ethylene In Plant Biology, (1992), pp. 176–181.

Morgan, M.E. Saltveit, J.R., "Introduction and Historical Perspectives", Ethylene In Plant Biology, (1991), pp. 1–13.

Mullis, K.B., et al, "Specific Synthesis of DNA in Vitro via a Polymerase–Catalyzed Chain Reaction", Methods in Enzymology, (1987), pp. 335–350.

Murashige, T. and Folke, S. "A Revised Medium For Rapid Growth and Bio Assays With Tobacco Tissue Cultures", Physiologia Plantarum, vol. 15, pp. 473–515 (1962).

Murray, A.J. "Expression of EFE Antisense RNA in Tomato Causes Retardation of Leaf Senscense and Most Fruit Ripening Characteristics", Cellular and Molecular Aspects of the Plant Hormone: Ethylene, (1993), pp. 327–328.

Nadeau, J. and O'Neill, S., "Nucleotide Sequence of a CDNA Encoding 1–Aminocyclopropane–1–Carboxylate Oxidase from Senescing Orchid Petals", Division of Biological Science, Plant Biology Section, (1995), pp. 833–834.

Nadeau, J., Zhang, X.S., Nair, H., and O'Neill, S. "Temporal and Spatial Regulation of 1–aminocyclopropane–1carboxylate Oxidase in the Pollination–induced Senescence of Orchid Flowers", Division of Biological Science, Plant Biology Section, (1993), pp. 31–39.

Nakagawa, et al, "Cloning of a Complementary DNA for Auxin–Induced 1–Aminocyclopropane–1–carboxylate Synthase and Differential Expression of the Gene by Auxin and Wounding", (1991) Plant Cell Physiol, 32; 1153–63.

Nakajima, N., et al, "Molecular Cloning and Sequence of a Complementary DNA Encoding 1–Aminocyclopropane–1–carboxylate Synthase Induced by Tissue Wounding", Plant Cell Physiology, (1990), pp. 1021–1029.

Nell, T., "Use and Care Advice", Geranium IV: The Grower's Manual, 4th Ed., (1991), Chapter 18, pp. 171–172.

Odell, et al., "Identification of DNA Sequences required for activity of the cauliflower mosaic virus 35S promoter", Nature 313:810–812 (1985).

Oeller, P.W., et al, "Reversible Inhibition of Tomato Fruit Senescence by Antisense RNA", Science, (1991), pp. 437–439.

Ohme–Takagi and Shinshi, "Ethylene–inducible Dna Binding Proteins That Interact with Ethylene Responsice Element", Plant Cell 7, (1995), pp. 173–182.

Olson, D.C., et al, "Differential Expression of two genes for 1–aminocyclopropane–1–carboxylate synthase in tomato fruits", Proceedings of National Academy of Sciences, (1991), pp. 5340–5344.

O'Neill, et al., "Interorgan regulation of Ethylene Biosynthetic Genes by Pollination", (1993) Plant Cell 5: 419–432.

Purk, K.Y., et al, "Molecular cloning of an 1–aminocyclopropane–1–carboxylate synthase fom senescing carnation flower petals", Plant Molecular Biology, (1992), vol. 18, pp. 377–386.

Paszkowski, et al., "Direct Gene Tranfer to Plants", EMBO Jounal 12:2717–2722 (1984).

Pogson B.J., et al., "Differential expression of Two 1–Aminocyclopropane–1–1carboxylic Acid Oxidase Genes in Broccoli after Harvest", (1995) Plant Physiol 108: 651–657.

Rando, R.R., "Chemistry and Enzymology of $K_{Cet}$ Inhibitors" (1974), Science 185, pp. 320–324.

Ranu, R.S., et al, "Regulation of Protein Synthesis in Rabbit Reticulocyte Lysates: Preparation of Efficient Protein Synthesis Lysates andthe Purification and Characterization of the Heme–Regulated Translational Inhibitory Protein Kinase", Methods in Enzymology, vol. 60, (1979), pp. 459–484.

Ranu, R.S., et al, "In Vitro Translation of the Full–Length RNA Transcript of Figwort Mosaic Virus (Caulimovirus)", Gene Expression, vol. 5, (1996), pp. 143–153.

Ranu R.S., "DNA Sequencing With Taq–DNA Polymrase", Biotechniques, (1995), pp. 390–395.

Reich et al., "Efficient Tranformation of Alfalfa Protoplasts by the intranuclear Microinjection of TI Plasmids", Bio/Technology, 4:1001–1004 (1986).

Reid & Men–Jen, "Ethylene and Flower Senescence", Plant Growth Regulation II, (1992), pp. 37–43.

Richins, et al., "Sequence of Figwort Mosaic virus DNA", Nucl. Acids Res. 15:8451–8466 (1987).

Rothstein, et al, "Stable and heritable inhibition of the expression of nopaline synthase in tobacco expressing antisense RNA", (1987) Proc. Natl. Acad. Sci. 84: 8439–8443.

Rottmann, W.H., et al, "Theologis: A 1–Aminocyclopropane–1–Carboxylate Synthase in Tomato Is Encoed by a Multigene Family Whose Transcription If Induced During Fruit and floral Senescence", Journal of Molecular Biology, (1991), pp. 937–961.

Sambrook J., Fritsch, E.F., and Maniatis, T., "Molecular Cloning: A Laboratory Manual", Cold Spring Harbor Laboratory Press (1989).

Sanders, et al., "Comparison of Cauliflower mosaic virus 35s and nopaline synthase promoters in transgenic plants", Nucl Acids Res. vol. 15, No. 4, pp. 1543–1558 (1987).

Sanger, F., et al, "DNA sequencing with chain–terminating inhibitors", Proc. Natl. Acad. Sci., (1977), pp. 5463–5467.

Sarin, et al., "Inhibition of acquired immunodeficiency syndrome virus by oligooxynucleoside methylphosphonates", (1988) Proc. Natl. Acad. Sci. U.S.A. 85:7448–7451.

Sato, et al, "Cloning the mRNA encoding 1–aminocyclopropane–1–carboxylate synthase, the key enzyme for ethylene biosynthesis in plants", Proceedings of the National Academy of Sciences, (1989), pp. 6621–6625.

Sato, Takahide, et al, "The 1–Aminocyclopropane–1–carboxylate Synthase of Cucurbita", The Journal of Biological Chemistry, vol. 286, (1991), pp. 3752–3759.

Schlagnhaufer, C.D., et al, "Molecular cloning of an ozone–induced 1–aminocyclopropane–1–carboxylate synthase cDNA and its relationship with a loss of rbcS in potato (Solanum tuberosum L.)", Plant Molecular Biology, (1995), pp. 93–103.

Schmulling, et al., "Promoters of the rolA, B and C Genes of Agrobacterium Rhizogenes are differentially regulated i transgenic plants", (1989), Plant Cell 1, pp. 665–670.

Shin, O.Y., Octiber, J.H., Yip, W.K., Yang, S.F. "The Promoter of Le–acs7, an Early Flooding–induced 1–Aminocyclopropane–i–Carboxylate Synthase Gene of the Tomato Is Tagged by a S013 Transposon", Proc. Nad. Acad. Sci., (1995), pp. 10334–10339.

Slater, A., et al., "Isolation and characterization of CDNA clones for Tomato polygalacturonase and other ripening related proteins", (1985), Plant Mol Bio vol. 15, pp. 137–147.

Smith, C.J.S., et al, "Antisense RNA inhibition of polygalacturonase gene expression in transgenic tomatoes", Letters to Nature, Nature, (1991), pp. 724–726.

Smith, T.F. and M.S. Waterman, "Indentification of Common Molecular Subsequences," J. Molecular Biology (1981), pp. 195–197.

Stein, et al., "Physiochemical properties of phosphorothioate oligodeoxynucleotides", (1988), Nucl. Acids Res. 16:3209–3221.

Stiekeman, et al., "Phytochrome control of the Expression to Two Nuclear Genes Encoding Chloroplast Proteins in Lemna Gibba L. G–3", (1983), Plant Physiol. 72:717–724.

Stockhaus, et al., "Identification of Enhancer elements in the Upstream region of the Nuclear Photosynthtic Gene ST–LS1", (1989), The Plant Cell 1:805–814.

Sugaya, et al., "Cell Specific Expression of the RolC Gene of the TL–DNA of Ri Plasmid in Transgenic Tobacco Plants", (1989), Plant Cell Physiol 30:649–654.

Theologis, A., et al, "Modifying Fruit Ripening by Supressing Gene Expression", Cellular and Molecular Aspects of the Plant Hormone Ethylene, (1993), pp. 19–23.

Thompson, et al., "Phytochrome control of RNA Levels in developing pca dn mung bean leaves", (1983), Planta 158:487–500.

US Application 08/724,194, filed Oct. 1, 1996, "1–aminocyclopropane–1–carboxylate Synthase Genes from Pelargonium to Control Ethylene Levels in Geraniums", 57 pages & 8 figures.

US Application 09/171,482, filed Oct. 19, 1998, "A 1–aminocyclopropane–1–carboxylate Synthase gene from Rosa to Control Ethylene Levels in Roses", 51 pages.

Van Der Straeten, et al, "Cloning, Genetic Mapping, and Expression Analysis of an Arabidopsis Thalinana Gene that Encodes 1–Aminocyclopropane–1 –Carboxylate Synthase", Proc Natl Acad Sci., (1992), pp. 9969–9973.

Van Der Stracten, D., et al, "Cloning and Sequence of two different cDNAs encoding 1–aminocyclopropane–1–carboxylate Synthase in a Tomato", Proceedings of the National Academy of Sciences, (1990), pp. 4859–4863.

Wang, and Woodson, "Nucleotide Sequence of a cDNA Encoding the Ethylene–Forming Enzyme from Petunia Corollas", Plant Physiology, (1992), pp. 535–536.

Wang, and Woodson, "A Flower Senescence–Related mRNA from Carnation Shares Sequence Similarity with Fruit Ripening–Related mRNAs Involved in Ethylene Biosynthesis", Department of Horticulture, Plant Physiology, (1991) pp. 1000–1001.

Wang, T.W. and Arteca, R.N., "Identification and Characterization of cDNAs Encoding Ethylene Biosynthetic Enzymes from Pelargonium X Hortorum CV Snow Mass Leaves", Plant Physiology, (1995), pp. 627–636.

Waterman, M.S. and Eggert, M. "A New Algorithm for Best Subsequence Alignments With Application to Trna–Rrna Comparison," J. Molecular Biology, (1987), pp. 723–728.

Wen, C.M., et al., "Nucleotide Sequence of a cDNA Clone Encoding 1–Aminocyclopropane–1–Carboxylate Synthase in Mustard", (1993), Plant Physiol 103:1019–1020.

Wu, R., et al., "Synthetic Oligodeoxynucleotides for Analyses of DNA Structure and Function", Prog. Nucl. Acid Res. Molec. Biol. 21:101–141 (1978).

Yang, S. F., et a, "Ethylene Biosynthesis and its Regulation in Higher Plants", Plant Physiology Annual Review (1984), pp. 155–189.

Yip, W.K., et al, "Differential Accumulation of Transcripts for Four Tomato 1–aminocyclopropane–1–carboxylate Synthase Homologs under Various Conditions", Proceedings of the National Academy of Sciences, (1992), vol. 89, pp. 2475–2479.

Zarembinski, T.I., et al, "Ethylene Biosynthesis and Action: A Case of Conservation", Plant Molecular Biology, (1994), pp. 1579–1597.

Zarembinski, T.I., et al., "Anaerobiosis and Plant Growth Hormones Induce Two Genes Encoding 1–Aminocyclopropane–1–carboxylate Synthase in Rice", (1993) Molecular Biology of the Cell, vol. 4: 363–373.

Zon, G., "Oligonucletotide Analogues as Potential Chemotherapeutic Agents", (1988), Pharmaceutical Research, vol. 5, no. 9:539–549.

US Provisional Patent Application No. 60/239, 782, filed Oct. 12, 2000, entitled "Partial Gene Sequences from Pelargonium to Control Ethylene Levels in Geraniums".

* cited by examiner pPHSacc25

GGGTTGCCGGGGTTCAGGATGGGCGTTATCTACTCCTAC
AACGAGAACGTGCTCACTACTGCCAAAAAGTTGACGAG
ATTTTCATCCATTTCAGCTCCGACGCAGCGCTTGCTCGT
CGTTATGCTCTCGGACACGCGGTTCACTCAAAAGTTCAT
CGAGGTAAACAGAGCGAAACTCAAAAGAATGTACGCTG
CATTCGTGGCGGGGGTTGAAGAAACTCGGCATCCGATG
CACGGAAAGCAGCGGAGGCTTCTCTATTGTTGGGCCGA
CATGAGCGGATTGATTCGATCCTACAGCGAAAAGGAG
AGCTCGAGCTATGGGACAAGTTGCTAAACATTGCTAAG
GTAAACGTTACTCCCGGTTCTTGTTGTCATTGTATTGAA
CCCGGCTACTTTAGCCTCTG

SEQUENCE LISTING

<160> NUMBER OF SEQ ID NOS: 3

<210> SEQ ID NO 1
<211> LENGTH: 404
<212> TYPE: DNA
<213> ORGANISM: Pelargonium

<400> SEQUENCE: 1

```
gggttgccgg ggttcaggat gggcgttatc tactcctaca acgagaacgt gctcactact      60
gccaaaaagt tgacgagatt ttcatccatt tcagctccga cgcagcgctt gctcgtcgtt     120
atgctctcgg acacgcggtt cactcaaaag ttcatcgagg taaacagagc gaaactcaaa     180
agaatgtacg ctgcattcgt ggcggggtt gaagaaactc ggcatccgat gcacggaaag      240
cagcggaggc ttctctattg ttgggccgac atgagcggat tgattcgatc ctacagcgaa     300
aaaggagagc tcgagctatg ggacaagttg ctaaacattg ctaaggtaaa cgttactccc     360
ggttcttgtt gtcattgtat tgaacccggc tactttagcc tctg                     404
```

<210> SEQ ID NO 2
<211> LENGTH: 23
<212> TYPE: DNA
<213> ORGANISM: Artificial Sequence
<220> FEATURE:
<223> OTHER INFORMATION: PCR Primer
<221> NAME/KEY: misc_feature
<222> LOCATION: (3), (6), (9), (12), (18), (21)
<223> OTHER INFORMATION: n=inosine

<400> SEQUENCE: 2

```
ggnytnccng gnttymgnrt ngg                                              23
```

<210> SEQ ID NO 3
<211> LENGTH: 23
<212> TYPE: DNA
<213> ORGANISM: Artificial Sequence
<220> FEATURE:
<223> OTHER INFORMATION: PCR Primer
<221> NAME/KEY: misc_feature
<222> LOCATION: (3), (5), (6), (15), (18)
<223> OTHER INFORMATION: n=inosine

<400> SEQUENCE: 3

```
canannckra asmanccnrs ytc                                              23
```

PARTIAL GENE SEQUENCE FROM PELARGONIUM TO CONTROL ETHYLENE LEVELS IN GERANIUMS

This application is a continuation-in-part of U.S. patent application Ser. No. 09/776,529, filed Feb. 2, 2001, which was a continuation of U.S. patent application Ser. No. 09/171,482, filed Oct. 19, 1998, issued as U.S. Pat. No. 6,184,449, which was the U.S. National Stage Patent Application of International Patent Application No. PCT/US97/17644, filed Sep. 30, 1997, which was a continuation-in-part of U.S. patent application Ser. No. 08/724,194, filed Oct. 1, 1996, issued as U.S. Pat. No. 5,824,875, and claims the benefit of U.S. Provisional Patent Application No. 60/239,782, filed Oct. 12, 2000, each hereby incorporated by reference.

BACKGROUND OF THE INVENTION

This invention relates to the field of compositions and methods for inhibiting the enzyme 1-aminocyclopropane-1-carboxylate (ACC) synthase in geranium thereby prolonging the shelf-life of cut flowers as well as reducing leaf yellowing and petal abscission during shipping and storage. Specifically, identification of the PHSacc-25 gene of geranium which may be used individually or in combination with previously identified ACC synthase genes for genetic modification of geranium.

A variety of factors cause wilting and natural abscission in flowers, particularly after a cutting of the plant or when flowers have been removed from the plant. Such factors include increased oxygen levels, wounding, chemical stress, and the plant's own production of ethylene. Of these factors, the plant's production of ethylene, has been shown to play a key role in natural senescence, the degenerative process which generally leads to controlled cell death in plants, but also in the degradation of flowers after they have been cut.

Ethylene, in all higher plants, is important to plant growth and development with respect to seed germination, seedling growth, flowering, and senescence (Abeles, F. B. et al. (1992), In: *Ethylene in Plant Biology,* Academic Press, New York, pp. 285–291; Morgan, M. E. Saltveit, J.R., "Introduction and Historical Perspectives", Ethylene In Plant Biology, (1991), pp.1–13; Yang, S. F., et al., "Ethylene Biosynthesis and its Regulation in Higher Plants", Plant Physiology Annual Review (1984), pp. 155–189). Ethylene production in plants can also be associated with trauma induced by mechanical wounding, chemicals, stress (such as produced by temperature and water amount variations), and by disease. Hormones can also stimulate ethylene production. Such ethylene, also sometimes called "stress ethylene", can be an important factor in storage effectiveness for plants. Moreover, exposure of plant tissue to a small amount of ethylene often may be associated with increased production of ethylene by other adjacent plants. This autocatalytic effect may be often associated with losses in marketability of plant material during storage and transportation (Abeles et al., supra; Yang et al., supra).

The ethylene biosynthetic pathway in plants was established by Adams and Yang (Adams, D. O., et al., "Ethylene biosynthesis: Identification of 1-aminocyclopropane-1-carboxylic acid as an intermediate in the conversion of methionine to ethylene", Proc. Nat'l Acad Sci USA 76: 170–174). The first step involves the formation of S-adenosyl-L-methionine (AdoMet) from methionine by S-adenosyl-L-methionine synthetase. AdoMet is then converted to 1-aminocyclopropane-1-carboxylate (ACC), the direct precursor of ethylene in higher plants. This conversion is catalyzed by ACC synthase (S-adenosyl-L-methionine methyl thioadenosine-lyase, EC4.4.1.14), the rate limiting step in the ethylene biosynthetic pathway. (See also Kionka, C., et al., "The enzymatic Malonylation of 1-aminocyclopropane-1-carboxylic Acid in Homogenates of Mung Bean Hypocotyls", Planta 162: 226–235, (1984); Amrhein, N., et al., "Identification of a Major Metabolite of the Ethylene Precursor 1-Aminocyclopropane-1-carboxylic Acid in Higher Plants.", Naturwissenschaften 68: 619–620 (1981); Hoffman, N. E., et al., "Identification of a 1-(malonylamino)cyclopropane 1-carboxylic acid as a major conjugate of 1-aminocyclopropane-1-carboxylic acid, an ethylene precursor in Higher Plants", (1982), Biochem. Biophys. Res. Common. vol. 104, no. 2, pp.765–770.

Knowledge of the biosynthetic pathway for ethylene formation has been fundamental in developing strategies for inhibiting ethylene production in plants. One approach has been to use chemical inhibitors to inhibit the synthesis or activity of ethylene, two of the most common being aminoethoxyvinylglycine and aminooxyacetic acid (Rand, R. R., "Chemistry and Enzymology of $K_{Cat}$ Inhibitors" (1974), Science 185, pp. 320–324) and in Ethylene in Plant Biology, (Abeles, F. B., et. al., Ethylene in Plant Biology., (1992), pp. 285–291). However, chemical methods find limited use because such methods are expensive and the beneficial effect they provide is generally only short-lived.

A second approach has been to over express ACC deaminase, an enzyme which metabolizes ACC, thereby eliminating an intermediate in the biosynthesis of ethylene (Klee, et al., "Control of Ethylene Synthesis by Expression of a bacterial enzyme in Trangenic Tomato plants.", (1991), Plant Cell 3: 1187–1193) (See also Theologis, A., et al., "Modifying Fruit Ripening By Supressing Gene Expression", Cellular and Molecular Aspects of the Plant Hormone Ethylene, (1993), pp. 19–23). Because ACC deaminase is a bacterial enzyme, it is heterologous, and thus, external to the plant. Thus, it is unlikely that this approach will yield a modification that will be stable from generation to generation.

Yet another approach involves attempts to genetically inhibit the production of the enzymes involved in the biosynthesis of ethylene or to inhibit the biosynthesis of the enzymes directly. This approach has the advantage of not only altering the way the plant itself functions irrespective of external factors but also of presenting a system which reproduces itself, that is, the altered plant's progeny will have the same altered properties for generations to come.

Initial efforts to better understand the enzymes which catalyze the reactions in the biosynthesis of ethylene have involved the identification and characterization of the genes encoding for AdoMet synthetase, ACC synthase, and ACC oxidase (See also Kende, H. et al., "Ethylene Biosynthesis: Annual Review of Plant Physiology", Plant Molecular Biology, (1993), pp. 283–307). Some of the genes encoding for ACC synthase have been identified for a number of plants. For instance, ACC synthase sequences have been identified for zucchini (Sato, et al., "Cloning the mRNA encoding 1-aminocyclopropane-1-carboxylate synthase, the key enzyme for ethylene biosynthesis in plants", Proceedings of the National Academy of Sciences, (1989), pp. 6621–6625), winter squash (Nakajima, N., et al., "Molecular Cloning and Sequence of a Complementary DNA Encoding 1-Aminocyclopropane-1-carboxylate Synthase Induced by Tissue Wounding", Plant Cell Physiology, (1990), pp. 1021–1029), tomato (Van Der Straeten, D., et al., "Cloning and Sequence of two different cDNAs encoding 1-aminocyclopropane-1-carboxylate Synthase in a Tomato", Proceedings of the National Academy of Sciences, (1990), pp. 4859–4863); (Rottmann, W. H., et al., "Theologis: A 1-Aminocyclopropane-i-Carboxylate Synthase in Tomato Is Encoded by a Multigene Family Whose Transcription Is Induced During Fruit and Floral Senescence", Journal of Molecular Biology, (1991), pp. 937–961), apple (Dong, J. G., et al., "Cloning of a cDNA Encoding 1-aminocyclopropane-1-carboxylate Synthase and Expression of its mRNA in Ripening Apple Fruit", Planta, pp. 38–45 (1991)), mung bean (Botella, J. R, et al., "Identification and Characterization of a Full-length cDNA Encoding for an Auxin-induced 1-aminocyclopropane-1-carboxylate Synthase from Etiolated Mung Bean Hypocotyl Segments and Expression of its mRNA in Reponse to Indole-3-acetic Acid", Plant Molecular Biol 20, pp. 425–436 (1992); Botella, J. R., et al., "Identification and characterization of three putative genes for 1-Aminocyclopropane-1-carboxylate Synthase from etiolated mung bean hypocotyl segments", Plant Mol Biol 18, pp. 793–797 (1992); Botella, J. R., et al., "Identification of two new members of the 1-Aminocyclopropane-1-carboxylate Synthase-Encoding Multigene family in mung bean", Gene 06852, pp. 249–253, (1993)); Kim W., et al., "Induction of 1-aminocyclopropane-1-carboxylate Synthase mRNA by Auxin in Mung Bean Hypocotyls and Cultured Apple Shoots", (1991), Plant Physiol 98:465–471), carnation (Park, K. Y., et al., "Molecular cloning of an 1-aminocyclopropane-1-carboxylate synthase from senescing carnation flower petals", Plant Molecular Biology, (1992), Vol. 18, pp. 377–386), *Arabidopsis thaliana* (Liang, X., et al., "The 1-aminocyclopropane-1-carboxylate synthase gene family of *Arabidopsis thaliana*", Proceedings of the National Academy of Sciences, (1992), pp. 11046–11050; Van Der Straeten, et al., "Cloning, Genetic Mapping, and Expression Analysis of an *Arabidopsis Thalinana* Gene that Encodes 1-Aminocyclopropane-1-Carboxylate Synthase", Proc. Natl. Acad. Sci., (1992), pp. 9969–9973.), tobacco, rice (Zarembinski, T. I., et al., "Anaerobiosis and Plant Growth Hormones Induce Two Genes Encoding 1-Aminocyclopropane-1-carboxylate Synthase in Rice", (1993) Molecular Biology of the Cell, Vol. 4: 363–373), mustard (Wen, C. M., et al., "Nucleotide Sequence of a cDNA Clone Encoding 1-Aminocyclopropane-1-Carboxylate Synthase in Mustard", (1993), Plant Physiol 103:1019–1020), orchid (O'Neill, et al., "Interorgan regulation of Ethylene Biosynthetic Genes by Pollination", (1993) Plant Cell 5: 419–432), broccoli (Pogson B. J., et al., "Differential Expression of Two 1-Aminocyclopropane-1-1carboxylic Acid Oxidase Genes in Broccoli after Harvest", (1995) Plant Physiol 108: 651–657), and potato (Schlagnhaufer, C. D., et al., "Molecular cloning of an ozone-induced 1-aminocyclopropane-1-carboxylate synthase cDNA and its relationship with a loss of rbcS in potato (*Solanum tuberosum* L.)", Plant Molecular Biology, (1995), pp. 93–103).

That ACC synthase is involved in the ethylene pathway is confirmed by the fact that increased levels of ACC synthase mRNA correlate with an increased activity of ACC synthase in plants during fruit ripening and flower senescence. Similar correlation is also observed in response to exogenous signals caused either by wounding or due to treatment with hormones such as auxin, cytokinin and ethylene. Interestingly, the expression of different classes of ACC synthase occurs from a variety of signals in a many plants, e.g. four different ACC synthase genes have been shown to be differentially expressed in tomato fruit, cell cultures, and hypocotyls during ripening, wounding, and auxin treatment (Olson, D. C., et al., "Differential expression of two genes for 1-aminocyclopropane-1-carboxylate synthase in tomato fruits", Proceedings of National Academy of Sciences, (1991), pp. 5340–5344; and Yip, W. K., et al., "Differential Accumulation of Transcripts for Four Tomato 1-aminocyclopropane-1-carboxylate Synthase Homologs under Various Conditions", Proceedings of the National Academy of Sciences, (1992), Vol. 89, pp. 2475–2479). Differential expression of two ACC synthase genes has also been observed in winter squash during wounding or by auxin (Nakajima, N., et al., "Molecular Cloning and Sequence of a Complementary DNA Encoding 1-Aminocyclopropane-1-carboxylate Synthase Induced by Tissue Wounding", Plant Cell Physiology, (1 990), pp. 1021–1029; and Nakagawa, et al., "Cloning of a Complementary DNA for Auxin-Induced 1-Aminocyclopropane-1-carboxylate Synthase and Differential Expression of the Gene by Auxin and Wounding", (1991) Plant Cell Physiol, 32; 1153–63). Similar differential regulation of ACC synthase gene expression takes place in carnation flowers by wounding, or during senescence (Park, K. Y., et al., "Molecular cloning of an 1-aminocyclopropane-1-carboxylate synthase from senescing carnation flower petals", Plant Molecular Biology, (1992), Vol. 18, pp. 377–386). The evolution of ACC synthase genes into a multigene family that responds differentially during plant development or in response to stimuli external to the plant (Rottmann, W. H., et al., "Theologis: A 1-Aminocyclopropane-i-Carboxylate Synthase in Tomato Is Encoded by a Multigene Family Whose Transcription Is Induced During Fruit and Floral Senescence", Journal of Molecular Biology, (1991), pp. 937–961) may be a reflection of the importance of ethylene in plants. (See also Slater, A., et al., "Isolation and characterization of cDNA clones for Tomato polygalacturonase and other ripening related proteins", (1985), Plant Mol Bio vol. 15, pp. 137–147; Smith, T. F. and M. S. Waterman, "Indentification of Common Molecular Subsequences," J. Molecular Biology (1981), pp. 195–197; and Smith, C. J. S., et al., "Antisense RNA inhibition of polygalacturonase gene expression in transgenic tomatoes", Letters to Nature, Nature, (1991), pp. 724–726; Hamilton, A J, et a, "Antisense Gene that Inhibits Synthesis of the Hormone Ethylene in Transgenic Plants", Nature, (1990), pp. 284–287).

The discovery of the foregoing and of other properties has lead to an understanding that it may be desirable to attempt to genetically alter the production of ethylene in plants. This approach, however, may be considered in some ways delicate. Elimination of ethylene is not a desired result as in many instances it will kill the plant. Modulation of ethylene—at the appropriate times—is the critical goal, not elimination of it entirely. Modulation of ethylene has been attempted with respect to at least two points in the pathway: 1) the production of ACC in response to ACC synthase, and 2) the oxidation of ACC in response to a different enzyme, ACC oxidase. Because regulation of production of ACC synthase in response to ACC synthase can permit stable modulation and not only total elimination of ethylene, it is a preferred technique. To date, however, successful reduction of the production of ethylene through an alteration at the ACC synthase step in the pathway has only been accomplished in one plant, tomato (Oeller, P. W., et al., "Reversible Inhibition of Tomato Fruit Senescence by Antisense RNA", Science, (1991), pp. 437–439). In spite of the seemingly simple conceptual nature of this goal, the actual accomplishment of an alteration of the ethylene biosynthetic pathway through the regulation of ACC synthase production has remained elusive. This is particularly true for the geranium plant, perhaps due to the fact that the identification of full length genes can be difficult for plants. As discussed later, this may, in part, be due to the fact that isolation of full length or high quality RNA has been deemed "notoriously difficult" for plants. (John, M. E., "An efficient method for isolation of RNA and DNA from plants containing polyphenolics", Nucleic Acids Research (1992), pp. 2381).

Efforts by others highlight some of the difficulty involved. Recently, Arteca's laboratory (Wang, T. W. and Arteca, R. N., "Identification and Characterization of cDNAs Encoding Ethylene Biosynthetic Enzymes from Pelargonium X Hortorum CV Snow Mass Leaves", Plant Physiology, (1995), pp. 627–636) studied two cDNA molecules encoding ACC synthase from a white flower variety of a flowering geranium plant (*Pelargonium x hortorum* cv Snow Mass Leaves). As their publication explained (perhaps after the fact), these researchers tried to identify and characterize two clones, GAC-1 and GAC-2. In spite of their efforts, they were only able to completely identify one of those cDNA gene sequences, GAC-1. Their study examined the expression of these ACC synthase genes in different plant parts of the geranium and in response to stress induced by osmotic changes (sorbitol) or metal ions ($CuCl_2$). It also evaluated the effects of ethylene on auxin 2,4-D induction in geranium leaves. The study indicated that GAC-1 expression was induced only by stress, whereas expression of GAC-2 appeared to be developmentally regulated. Furthermore, these authors speculated about possible future "transfer of antisense GAC-1, GAC-2 . . . into Pelargonium tissues through the Agrobacterium transformation or particle bombardment." This confirms a desire in the art for an ACC synthase approach to altering ethylene production in such plants. In spite of this desire, however, the isolation and identification of some, if not all, the ACC synthase gene sequences—for geranium remained elusive.

Although several plant ACC synthase genes have been identified and sequenced, the current invention describes ACC synthase gene sequences which were previously unknown and which are not believed to have been easily discoverable. As mentioned, one factor which may have militated against an expectation of successfully cloning a plant gene is the particular difficulty in obtaining high-quality and full-length RNA from plants. Indeed, this process has been characterized as "notoriously difficult" by at least more than one practitioner of the art (John, M. E., "An efficient method for isolation of RNA and DNA from plants containing polyphenolics", Nucleic Acids Research (1992), pp. 2381 and Logemann, J., et al., "Improved Method for the Isolation of RNA from Plant Tissues", Analytical Biochem (1987), pp. 16–20)). While this proved to be true for the present inventor, these difficulties were overcome by assessing a new approach to the RNA isolation process. The current inventor, after finding traditional RNA isolation methods to be ineffective, was forced to develop a non-traditional approach described herein. Basically, even though those of ordinary skill in the art had long desired to identify some gene or portion of a gene to manipulate to alter the production of ethylene in some plants, in this case, they failed to realize that the problem lay in the need for a better isolation process. Even though the implementing technology for this process had long been available, those in the art apparently failed to realize how to use that technology to achieve the results now described. To some extent they simply may not have defined the problem, preventing the achievement of the goals sought. Their efforts may properly be characterized as having taught away from the direction taken by the present inventor and, thus, the results achieved here should be considered unexpected.

Difficulties in isolating full-length mRNA in this specific case are also further reflected by the fact that one of the sequences isolated by the current inventor (clone pPHSacc49), though it may bear some similarity to portions of the clone termed GAC-2 by Wang et al., supra, (which, in any case, may have been discovered after the making of the present invention) is actually considerably longer than GAC-2. This highlights the difficulty in successfully isolating a full-length mRNA molecule using standard RNA isolation procedures in certain plant materials. Furthermore, the current inventor has previously isolated a third novel full-length clone (pPHSacc44). Moreover, the high quality RNA (as defined below) isolated by the current inventor is further evidenced by the fact that full length cDNA clones were obtained for pPHSacc44 and pPHSacc49, and all of them could be successfully expressed in an in vitro expression system. In each case, full length ACC synthase (enzyme) protein was synthesized in vitro. In contrast, even later publications by Arteca's group do not describe the actual in vitro expression of any of the isolated DNA clones.

This is significant because it highlights the difficulty in identifying full length ACC synthase genes. Derivation of DNA encoding ACC synthase from a genomic clone rarely is successful, and therefore, simply would not provide a reasonable expectation of success to one of ordinary skill. Only by utilizing a new and different approach did the present invention successfully identify not only one but several full length ACC synthase gene sequences, and the partial sequence which comprises the instant invention, from the geranium plant. Basically, it was this high quality library containing full length cDNA clones which allowed the present inventor to successfully achieve direct cloning of ACC synthase cDNA. The prior art did not discover these sequences because it could not have: the genes did not exist in the available libraries. It was this new approach which overcame the problems faced, but not solved, by others and resulted in the extraordinary successes described herein. Mere comparison to other genes in the same or different plants did not and could not have yielded the successes described here. The existence of the cDNAs of interest in the library was the governing factor. Thus, even with a viable identification process, successful identification of the several geranium ACC synthase genes, let alone the actual alteration of the plant itself by means of this knowledge, would not have been likely.

Additionally, it should be understood that knowledge of the full DNA sequence of a gene from other plants simply does not lead one to the sequences of the homologous genes in the geranium plant. First, as mentioned earlier, the genes encoding ACC synthase have evolved into a multigene system. There appears to be no single gene, but rather a family of genes in most cases. Thus, knowledge of one gene in one plant species is not certain to lead to one (or several) homologous or analogous genes in another plant species. Second, because known ACC synthase genes are typically so diverse in their nucleotide sequences, knowledge of one would not lead a person of ordinary skill in the art to an expectation of success in isolating the ACC synthase from geranium.

Antisense technology is a well known approach to creating a plant that produces less of a selected protein. Through this technology, a plant is altered by introducing a foreign DNA sequence that encodes an mRNA product complementary to part or all of the plant's "sense" mRNA encoding the protein. The presence of antisense RNA inhibits RNA function within a cell (and whole organism). Antisense RNA can bind in a highly specific manner to its complementary sense RNA resulting in blockade in processing or translation of the sense mRNA. Antisense RNA may also disrupt interactions between sense mRNA and sequence-specific RNA binding proteins. Antisense technology may be employed to inhibit the synthesis of an enzyme involved in ethylene biosynthesis. The partial gene sequence identified by the current inventor and disclosed herein may be used for the conception of antisense sequences specific for ACC synthase mRNA. Introduction of the DNA encoding such antisense RNA sequences into a geranium plant results in a plant which may stably produce less ethylene.

The incorporation of antisense RNA in plants as a means to inhibit the synthesis of enzymes has been described by various investigators. Rothstein, et al, "Stable and heritable inhibition of the expression of nopaline synthase in tobacco expressing antisense RNA", (1987) Proc. Natl. Acad. Sci. 84: 8439–8443, found that antisense RNA inhibited nopaline synthase (nos) in tobacco.Smith, C. J. S., et al, "Antisense RNA inhibition of polygalacturonase gene expression in transgenic tomatoes", Letters to Nature, Nature, (1991), pp. 724–726, reported that antisense RNA inhibited polygalacturonase in tomato. Others have used antisense RNA to inhibit the synthesis of enzymes involved in ethylene formation. (Oeller, P. W., et al., "Reversible Inhibition of Tomato Fruit Senescence by Antisense RNA", Science, (1991), pp. 437–439), expressed RNA antisense to ACC synthase in tomato plants. Others have expressed antisense RNA to a different ethylene forming enzyme (EFE), ACC oxidase, in carnation and tomato. (Michael, M. Z., et al, "Cloning of Ethylene Biosynthetic Genes Involved in Petal Senescence of Carnation and Petunia, and their Antisense Expression in Transgenic Plants", Cellular and Molecular Aspects of the Plant Hormone: Ethylene, (1993), pp. 298–303); Hamilton, A J, et a, "Antisense Gene that Inhibits Synthesis of the Hormone Ethylene in Transgenic Plants", Nature, (1990), pp. 284–287; Gray, J. E., et al, "Altered Gene Expression, Leaf Senescence, and Fruit Ripening by Inhibiting Ethylene Synthesis with EFE-Antisense Genes", Cellular and Molecular Aspects of the Plant Hormone Ethylene, pp. 82–89, (1993); Murray, A. J. "Expression of EFE Antisense RNA in Tomato Causes Retardation of Leaf Senescense and Most Fruit Ripening Characteristics", Cellular and Molecular Aspects of the Plant Hormone: Ethylene, (1993), pp. 327–328). The above work with antisense RNA may also be applicable to efforts to stably incorporate the partial gene sequence identified by the current inventor and their antisense sequences into geranium plants. Similarly, the success in expressing antisense RNA for ACC synthase in tomato plants may also be applicable (Oeller, et al., supra). It is noteworthy, and perhaps surprising, that neither of the foregoing disclosures have led to the long sought goal of stably altering ethylene production in geranium plants. Hence, an altered geranium plant expressing reduced levels of ethylene has not been described. The incorporation of ACC synthase antisense DNA into a geranium plant has remained elusive because the complete ACC gene sequences were not available prior to the present invention. The discoveries disclosed herein enable the production of an appropriately altered geranium plant expressing ACC synthase antisense sequences and stably producing reduced levels of ethylene.

SUMMARY OF THE INVENTION

The broad object of the invention can be to provide a method for genetic modification of geranium plants (or may be applicable to other plants as well) to control their levels of ethylene. Controlling the level of ethylene in geranium plants may comprise the use of the instant invention individually as disclosed below, or in combination with previously identified genes from geranium or rose for which the full length DNA sequences have also been previously disclosed, or in combination with geranium promoter sequences. See, 1-Aminocyclopropane-1-carboxylate Synthase Genes From Pelargonium, U.S. Pat. No. 5,824,875; 1-Aminocyclopropane-1-Carboxylate Synthase Genes From Pelargonium And Rosa To Control Ethylene Levels In Geraniums And Roses, PCT Patent Application No. PCT/US97/17644; 1-Aminocyclopropane-1-Carboxylate Synthase Genes From Rosa To Control Ethylene Levels In Roses, U.S. National Phase Application No. 09/171,482; and Plant Promoter, U.S. Patent Application No. 60/203021, each hereby incorporated by reference. The instant invention used individually or in combination with such disclosed DNA molecules, fragments thereof, or combinations of such molecules or fragments, may be introduced into a plant cell in reverse orientation to inhibit expression of ACC synthase, thereby reducing the levels of endogenous ethylene.

Another broad object of the invention is to produce transgenic plants which may be monitored for growth and development. Those plants exhibiting prolonged shelf-life with respect to plant growth, flowering, or reduced yellowing of leaves due to reduction in levels of ethylene are to be selected and propagated as premier products with improved properties including reduced leaf yellowing and petal abscission during shipping and storage.

The present invention comprises the identification of the PHSacc-25 gene of geranium which encodes for ACC synthase enzyme or a functional derivative of the gene. The invention further comprises an isolated cDNA molecule having sequence homologous to the PHSacc-25 gene DNA sequence which encodes the ACC synthase enzyme of geranium or a functional derivative.

The invention further comprises the identity of a portion of the isolated cDNA molecule (SEQ ID NO:1).

In another embodiment, the present invention provides the protein encoded by the cDNA molecule as described above, or a functional derivative thereof.

Also provided herein is an antisense oligonucleotide or polynucleotide which may encode an RNA molecule which is complementary to at least a portion of an RNA transcript of the ACC synthase gene described above, which RNA molecule hybridizes with the RNA transcript such that expression of the ACC synthase enzyme is altered.

The above antisense oligonucleotide or polynucleotide molecule can be full length or preferably has between six and 100 nucleotides.

The antisense oligonucleotide or polynucleotide may be complementary to at least a portion of one strand of the cDNA.

An antisense oligonucleotide as described above may be complementary to at least a part of the cDNA sequence SEQ ID NO:1 which part is, for example, from nucleotides 1–50; nucleotides 51–100; nucleotides 101–150; nucleotides 151–200; nucleotides 201–250; nucleotides 251–300; 301–350; or 351–400, and so forth.

In one embodiment, the antisense oligonucleotide can be complementary to at least a part of a 5' non-coding portion of one strand of the isolated cDNA molecule.

This invention can be further directed to a vector useful for transfection of a geranium plant cell, comprising:

(a) an antisense oligonucleotide or polynucleotide as described above;

(b) regulatory sequences required for expression of the oligonucleotide or polynucleotide in the cell.

The regulatory sequences comprise a promoter active in the cell, which may be an inducible promoter or preferably, a constitutive promoter. The vector preferably further comprise a polyadenylation signal.

In the above vector, the promoter is preferably a heterologous promoter such as a viral promoter. A preferred viral promoter is the CaMV 35S promoter or a promoter homologous to CaMV35S.

In other embodiments, the promoter is selected from the group consisting of the SSU gene promoter, ribulose bisphosphate carboxylase promoter, chlorophyll a/b binding protein promoter, potato ST-LS1 gene promoter, soybean heat shock protein hspl7.5-E promoter, soybean heat shock protein hspl7.3-B promoter, phenylalanine ammonia-lyase promoter, petunia 5-enolpyruvylshikimate-3-phosphate synthase gene promoter, *Rhizobium meliloti* FIXD gene promoter and nopaline synthase promoter, or the naturally occurring promoter for the geranium ACC synthase gene itself.

The invention can also provide a geranium cell transformed with such a vector as described above, a plantlet or mature geranium plant regenerated from such a cell, or a plant part from such a plant.

The present invention is further directed to a method to alter expression of an ACC synthase enzyme in a geranium cell, plant or a cutting thereof, comprising (a) transforming a geranium cell or plant with a vector according to any of the prior directions; and (b) allowing the antisense oligonucleotide or polynucleotide to be expressed and to hybridize with nucleic acid molecules in the cell, plant, or cutting which encode for the ACC synthase enzyme.

Also provided is a method of producing a geranium plant having reduced ethylene production compared to an unmodified geranium plant, comprising the steps of:

(a) transforming a geranium plant with a vector as above;

(b) allowing the plant to grow to at least a plantlet stage;

(c) testing the plant for ACC synthase enzymatic activity or ethylene production; and (d) selecting a plant having altered ACC synthase activity and/or altered ethylene production compared to an unmodified geranium plant.

A geranium plant produced as above, or progeny, hybrids, clones or plants parts thereof, preferably exhibits reduced ACC synthase expression and reduced ethylene production.

In another embodiment, the invention is directed to a method for producing a geranium variety (or line), characterized by reduced expression or activity of an ACC synthase enzyme and reduced ethylene production compared to an unmodified geranium variety, comprising producing a geranium plant as above and selfing the plant to generate the variety.

Also provided is a method for producing a variant plant of a non-geranium species, an ACC synthase genes of which is homologous to a geranium ACC synthase gene, in which variant plant the ACC synthase expression is altered in comparison to an unmodified plant of the species, comprising (a) identifying and isolating an ACC synthase gene of the species by hybridization with a sense DNA molecule as described above (b) constructing a vector which comprises an antisense DNA sequence encoding at least a part of the gene identified in step (a) in an antisense orientation such that (i) an RNA transcript of the antisense DNA sequence is complementary to the part of the gene, and (ii) expression of the antisense DNA sequence alters expression of the ACC synthase gene;

(c) transforming a cell of a plant of the species with the vector of step (b) to generate a transformed cell; and (d) regenerating a plant from the transformed cell of step (c), to produce the variant plant.

The above method is also used to produce a plant variety in a non-geranium plant species characterized by reduced expression or activity of an ACC synthase enzyme and reduced ethylene production compared to a conventional variety of the species, comprising producing a variant plant as above, and selfing the plant to generate the variety.

This invention also provides a method for genetically altering a plant, preferably a plant of a low RNA species, comprising the steps of:

(a) isolating mRNA of the plant using the 2-butoxyethanol precipitation technique wherein at least about 3–5 grams of plant tissue starting material is used to attain a critical mass amount of RNA for precipitation;

(b) constructing a cDNA library from the isolated mRNA (c) identifying and cloning a desired DNA sequence from the library (d) genetically altering the cloned DNA sequence;

(e) transforming cells of the plant or the plant directly with the altered DNA sequence; and (f) if done through a cell-based technique, reproducing a plant from the cells which plant expresses the altered DNA sequence, thereby genetically altering the plant.

In the above method, the plant is preferably a species of the genus Pelargonium or Rosa, most preferably a geranium plant. In the above method, the cloned DNA sequence preferably encodes ACC synthase.

The above method is used to produce a genetically altered geranium plant, comprising the steps of:

(a) isolating geranium mRNA using a 2-butoxyethanol precipitation technique wherein at least about 3–5 grams of plant tissue starting material is used to attain a critical mass amount of RNA for precipitation;

(b) constructing a cDNA library from the isolated mRNA (c) identifying and cloning at least one DNA sequence from the library (d) genetically altering the cloned DNA sequence;

(e) transforming geranium cells with the altered DNA sequence; and (f) regenerating the genetically altered geranium plant from the cells, which plant expresses the altered DNA sequence.

The invention is further directed to a method of isolating plant mRNA, comprising the steps of:

(a) extracting nucleic acids from a sufficient amount of plant tissue starting material to attain a critical mass amount of RNA for precipitation;

(b) isolating RNA from the nucleic acids of step (a) using a 2-butoxyethanol precipitation technique;

(c) contacting the RNA with a binding partner for mRNA, for example oligo-dT or another molecule or entity which has the characteristics of binding specifically to mRNA with the exclusion of other forms of RNA or DNA. The binding partner may be immobilized on a solid phase or carrier; this yields immobilized mRNA; and (d) eluting the immobilized mRNA from the carrier by conventional elution methods, or obtaining bound mRNA, thereby isolating the mRNA from total RNA.

BRIEF DESCRIPTION OF THE DRAWINGS

FIG. 3 shows the nucleotide sequence of a portion of the cDNA clone designated pPHSacc25 (SEQ ID NO:1).

DESCRIPTION OF THE PREFERRED EMBODIMENTS

Figure 1:
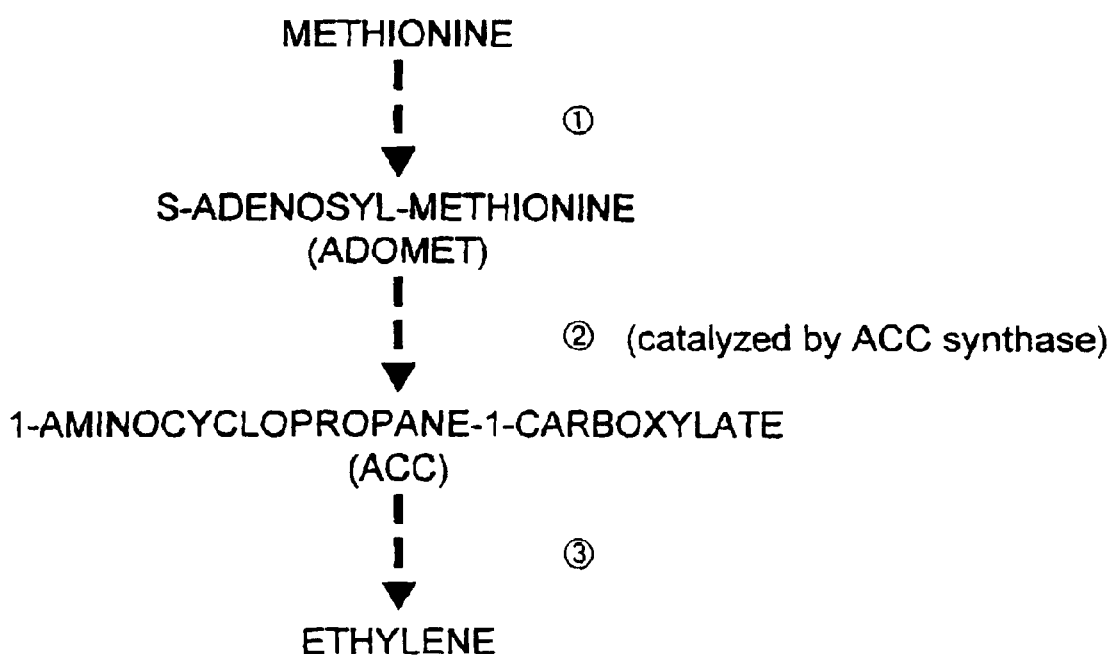
FIG. 1 shows the ethylene biosynthetic pathway including the step catalyzed by ACC synthase.

The present inventor has identified a novel ACC synthase gene in geranium (PHSacc-25). PHSacc-25 was identified by amplifying isolated mRNA using polymerase chain reaction, the resulting cDNAs were cloned into a plasmid, positive clones were isolated, and the cDNA insert was partially sequenced. A portion of the DNA sequence encoding for the enzyme ACC synthase in geranium plants (specifically from *Pelargonium hortorum* cv Sincerity) was identified. The cDNA sequence corresponds to a gene which may be important in the control of ethylene production.

The cloned ACC synthase gene fragments, can be introduced in reverse orientation (antisense) under control of a strong promoter (discussed below in detail), such as the cauliflower mosaic virus promoter CaMV35S, or the naturally occurring geranium promoter for that gene, to genetically modify a geranium plant. One result of this modification can be a reduction in the amount of translatable ACC synthase-encoding mRNA. As a consequence, the amount of ACC synthase produced in the plant cells may be reduced, thereby reducing the rate of conversion of ACC to ethylene. This genetic modification may effect a permanent change in ethylene levels in the modified plant and be propagated in offspring plants. Hence, the invention can provide a plant modified as described herein as well as plants which although modified in a different manner achieve similar results or utilize similar concepts as disclosed herein. The genetically altered plant may be used to produce a new variety or line of plants wherein the alteration is stably transmitted from generation to generation.

The geranium plant is one of the most ethylene-sensitive flowering plants (Nell, T., "Use and Care Advice", Geraniums IV: The Grower's Manual, 4th Ed., (1991), Chapter 18, pp 171–172). A change in ethylene levels may thus have a great impact on its commercial desirability. The present invention provides an isolated ACC synthase gene fragment obtained specifically from geranium for use in genetic modification preferably of geranium plants. The isolated DNA molecules described herein are unique to geraniums and vary significantly in sequence from ACC synthase DNA in any other unrelated plant species.

Because of such interspecies variation, to achieve stable genetic modification, it may be important that an ACC synthase gene or gene fragment (a) be obtained from the same species or (b) be a functional derivative of the DNA sequence native to the species. However, it may be possible that a selected sequence from one plant genus or species may be employed using antisense technology in a different genus or species to achieve a useful effect such as that described here. The present invention thus provides for the first time the appropriate DNA sequences which may be used to achieve a stable genetic modification primarily of geranium plants (and of other plants as well).

The identification, preparation of plasmid DNA, restriction enzyme digestion, agarose gel electrophoresis of DNA, Southern blots, Northern blots after separation of the RNA on a formaldehyde agarose gel, DNA ligation, and bacterial transformation were carried out using methods well-known in the art. See, for example, Sambrook, J., Fritsch, E. F., and Maniatis, T., "Molecular Cloning: A Laboratory Manual", Cold Spring Harbor Laboratory Press (1989)

As used herein, the term "plant" refers to either a whole plant, a plant part, a plant cell, or a group of plant cells. The types of plants which can be used in the method of the invention generally includes the genus Pelargonium (geraniums) which can take up and express the DNA molecules of the present invention. It may include plants of a variety of ploidy levels, including haploid, diploid, tetraploid, and polyploid.

A "transgenic plant" is defined as a plant which is genetically modified in some way, including but not limited to a plant which has incorporated heterologous DNA or modified DNA or some portion of heterologous or homologous DNA into its genome. The altered genetic material may encode a protein, comprise a regulatory or control sequence, or may comprise an antisense sequence or encode an antisense RNA which is antisense to an endogenous DNA or mRNA sequence of the plant.

A "transgene" or a "transgenic sequence" is defined as a foreign or atypical gene or partial sequence which has been incorporated into a transgenic plant.

As used in the present application, the term "substantial sequence homology" or "substantially homologous" is used to indicate that a nucleotide sequence (in the case of DNA or RNA) or an amino acid sequence (in the case of a protein or polypeptide) exhibits substantial functional or structural equivalence with another nucleotide or amino acid sequence. Any functional or structural differences between sequences having substantial sequence homology will be de minimis; that is, they will not affect the ability of the sequence to function as indicated in the desired application. Differences may also be simply due to inherent variations in codon usage among different species. Sequences that have substantial sequence homology with the sequences disclosed herein are usually "variants" of the disclosed sequence, such as mutations, but may also be synthetic sequences. Structural differences are considered de minimis if there is a significant amount of sequence overlap or similarity between two or more different sequences or if the different sequences exhibit similar physical characteristics even if the sequences differ in length or structure. Such characteristics include, for example, ability to hybridize under defined conditions, or, in the case of proteins, immunological cross reactivity, similar enzymatic activity, etc.

Additionally, two nucleotide sequences are substantially homologous if the sequences have at least 70 percent, more preferably 80 percent and most preferably 90 percent sequence similarity between them. Two amino acid sequences are substantially homologous if they have at least 50 percent, preferably 70 percent, and most preferably 90 percent similarity between the active portions of the polypeptides.

The term "hybridization" as used herein is generally understood to mean hybridization at appropriate conditions of stringency as would be readily evident to those skilled in the art depending upon the nature of the probe sequence and target sequences. Conditions of hybridization and washing are well-known in the art, and the adjustment of conditions depending upon the desired stringency by varying incubation time and temperature and ionic strength of the solution are readily accomplished. See, for example, Sambrook, J., Fritsch, E. F., and Maniatis, T., "Molecular Cloning: A Laboratory Manual", Cold Spring Harbor Laboratory Press (1989)). The choice of conditions is dictated by the length of the sequences being hybridized, in particular the length of the probe sequence, the relative G-C content of the nucleic acid and the amount of mismatches to be permitted. Low stringency conditions are preferred when partial hybridization between strands that have lesser degrees of complementarity is desired. When perfect or near-perfect complementarity is desired, high stringency conditions are preferred. For typical high stringency conditions, the hybridization solution contains 6×SSC, 0.01M EDTA, 5×Denhardt's solution and 0.5% SDS. Hybridization is carried out at about 68° C. for 3–4 hours for fragments of cloned DNA and 12–16 hours for total eukaryotic DNA. For lower stringency, the temperature is reduced to about 12° C. below the melting temperature ($T_m$) of the duplex. The $T_m$ is known to be a function of G-C content and duplex length as well as the ionic strength of the solution.

By "functional derivative" of a nucleic acid (or poly- or oligonucleotide) is meant a "fragment," "variant," "homologue" or "analogue" of the gene or DNA sequence encoding ACC synthase, or in some way related to the production or use of ACC synthase, especially geranium ACC synthase. A functional derivative may retain at least a portion of the function of the ACC synthase-encoding DNA which permits its utility in accordance with one embodiment of the present invention. Such function may include the ability to hybridize with native geranium or homologous DNA from another plant which encodes ACC synthase or with an mRNA transcript thereof, or, in antisense orientation, to inhibit the transcription and/or translation of geranium ACC synthase mRNA, or the like.

A "fragment" of the gene or DNA sequence refers to any subset of the molecule, that is, a shorter polynucleotide- or oligonucleotide. A "variant" refers to a molecule substantially similar to either the entire gene or a fragment thereof, such as a nucleotide substitution variant having one or more substituted nucleotides but which maintains the ability to hybridize with the particular gene or to encode a mRNA transcript which hybridizes with the native DNA. A "homologue" refers to a fragment or variant sequence from a different plant genus or species. An "analogue" refers to a non-natural molecule substantially similar to or functioning in relation to either the entire molecule, the variant, or to a fragment thereof.

"Altered" expression" or an "alteration" of expression of a gene (most particularly of ACC synthase), as used herein, refers to any process or result whereby the normal expression of the gene, for example that occurring in an "unmodified" geranium plant, defined as a known, conventional, naturally-occurring geranium plant, is changed in some fashion. As intended herein, an alteration is a complete or preferably a partial reduction in the expression of ACC synthase, but may also include a change in the timing of expression, or another state wherein the expression of ACC synthase differs from that which would be most likely to occur naturally in an unmodified geranium plant, variety or cultivar. A preferred alteration is one which results in a decrease in ethylene production by the plant compared to ethylene production in an unmodified plant.

In producing a genetically altered plant according to this invention, it is preferred to select individual plantlets or plants by the desired trait, generally reduced ACC synthesis expression and reduced ethylene production. Expression of ACC synthase can be measured by quantitating the amount of ACC synthase mRNA using conventional hybridization techniques. Alternatively, the amount of ACC synthase protein can be quantitated, for example in a conventional immunoassay method using a specific antibody such as those described herein. Finally, the ACC synthase enzymatic activity can be measured using biochemical methods as described in Kionka et al., supra; Amrhein et al, supra; or Hoffman N. E., et al., supra. Ethylene biosynthesis in the plantlet or plant can be quantitated using known methods Yang, S. F., et a, "Ethylene Biosynthesis and its Regulation in Higher Plants", Plant Physiology Annual Review (1984), pp. 155–189); Abeles, F. B. et al. eds, *Ethylene in Plant Biology*, Academic Press, New York, 1976; Nell, T., "Use and Care Advice", Geraniums IV: The Grower's Manual, 4th Ed., (1991), Chapter 18, pp 171–172).

In order for a newly inserted gene or DNA sequence to be expressed, resulting in production of the protein which it encodes (or, in the case of antisense DNA, to be transcribed, resulting in an antisense RNA molecule), the proper regulatory signals should be present in the proper location with respect to the coding or antisense sequence. These regulatory signals may include a promoter region, a 5'-non-translated leader sequence and a 3'-polyadenylation sequence as well as enhancers and other known regulatory sequence. The promoter is a DNA sequence that directs the cellular machinery to transcribe the DNA to produce RNA. The promoter region influences the rate at which the mRNA product and, if the DNA encodes a protein, the resultant protein product, are made. The 3'-polyadenylation signal is a non-translated region that functions in plant cells to cause the addition of a polyadenylate stretch to the 3'-end of the mRNA to stabilize it in the cytoplasm for subsequent translation. A promoter DNA sequence is operably linked to a second DNA sequence and regulates its transcription. If the second DNA sequence encodes a protein, the promoter DNA sequence is said to be "operably linked" if it affects the transcription of the mRNA encoding the protein product from the second DNA sequence. A DNA sequence comprising a promoter is generally physically near the coding sequence in the same recombinant construct, though physical contiguity is not required. "Strong" promoters are able to direct RNA synthesis at higher rates than weaker promoters. Certain promoters direct RNA production at higher levels only in particular types of cells and tissues. Promoters that direct RNA production in many or all tissues of a plant without the need for "induction" by a specific inducer substance are called constitutive promoters. The operation of a constitutive promoter is relatively independent of the developmental stage of the cell in which it is contained and is most preferred for the present invention. An inducible promoter is one which, in response to the presence of an inducer, is activated. Hence, a coding sequence driven by an inducible promoter can be turned on or off by providing or withdrawing the inducer. A promoter may be homologous, derived from the same species as the coding sequence. Preferably, the promoter is heterologous, that is, derived from another species, or even from a virus.

Expression levels from a promoter which is useful for the present invention can be tested using conventional expression systems, for example, by measuring levels of a reporter gene product (protein or mRNA) in extracts of the leaves, stems, roots and flowers of a transgenic plant into which the promoter/reporter have been introduced.

Cauliflower mosaic virus (CaMV) is a double-stranded DNA plant virus. It contains two promoters responsible for the production of transcripts of 35S and 19S in size in infected plants (Guilley, H., et al., "Transcription of cauliflower mosaic virus DNA: Detection of Promoter Sequences, and Chracterization of Transcripts", Cell, vol 30, pp. 763–773 (1982)). The 35S promoter (CaMV35S) is one of the strongest constitutive heterologous promoters known in plants (Odell, et al., "Identification of DNA Sequences required for activity of the cauliflower mosaic virus 35S promoter", Nature 313:810–812 (1985)); Jensen, J. S., et al., "Nodule-specific expression of a chimaeric soybean leghaemoglobin gene in transgenic *Lotus Corniculatus*", Nature 321:669–674 (1986); Jefferson, et al., "GUS Fusions: B-glucuronidase as a sensitive and versitile gene fusion marker in higher plants", EMBO J. 6:3901–3907 (1987); Kay, et al., *Science* 236:1299–1302 (1987); Sanders, et al., "Comparison of Cauliflower mosaic virus 35S and nopaline synthase promoters in transgenic plants", Nucl. Acids Res. vol. 15, no. 4, pp. 1543–1558 (1987)). Two different domains within the CaMV 35S promoter may differentially regulate expression of a coding sequence in different plant tissues (domain A, from nucleotides −90 to +8) vs. domain B from nucleotides -343 to -90), as described by Benfey, et al., "The CaMV 35S Enhancer Contains Atleast Two Domains Which Can Confer Different Developemental and Tissue Specific Expression Patterns" EMBO J. 8: 2195–2202 (1989). The CaMV35S promoter is active in isolated protoplasts (Fromm, M., et al., *Proc. Natl. Acad. Sci. USA* 82:5824 (1985)) and is expressed in all organs of various transgenic plants in the absence of any viral protein, making it widely used in plant genetic engineering.

Because of variability in the expression of genes driven by the CaMV35S promoter, (which may be either an intrinsic property of the promoter or a result of variability in the position at which CaMV35S promoter-driven DNA sequence is integrated into the genome of the transformed plant), CaMV35S may be particularly useful for effecting different degrees of altered gene expression by an antisense sequence which the promoter controls. Additional useful plant promoters in, for example, other caulimoviruses (a group of double-stranded DNA viruses to which the cauliflower mosaic virus belongs) have also been developed and are useful for similar applications. Two caulimoviruses distantly related to CaMV are the figwort mosaic virus (FMV) (Richins, et al., "Sequence of Figwort Mosaic virus DNA", Nucl. Acids Res. 15:8451–8466 (1987)) and the carnation etched ring virus (CERV) Hull, et al., "The Sequence of carnation etched ring virus DNA: comparison with cauliflower masaic virus and retroviruses", The EMBO Journal, vol 5. no. 12, pp. 3083–3090 (1986). The promoters of FMV and CERV which are homologues of the CaMV35S promoter are described in Rogers, U.S. Pat. No. 5,378,619. Any of the foregoing viral promoters, as well as other viral promoters which act as strong promoters for expression of plant DNA sequences in plant cells, may be used to drive the expression of the DNA molecule of the present invention.

Certain other strong plant promoters are also useful to direct the expression of the ACC synthase DNA (or antisense sequences) of the present invention. For example, the small subunit (SSU) of the enzyme ribulose-1,5-bisphosphate carboxylase (RuBPCase), the primary enzyme of the carbon fixation pathway in chloroplasts of plants of the C3 class is an example of a polypeptides known to be highly expressed in plants. A highly efficient SSU promoter DNA such as the promoter DNA from the SSU gene denominated SSU301 from Petunia (Bedbrook, et al., U.S. Pat. No. 4,962,028) may be used herein. The promoter may be used in the form of an isolated 5'-fragment of the SSU gene, and preferably has the 3'-end of the fragment modified to create a restriction site which permits ready fusions with the ACC synthase antisense DNA of the present invention. The promoter may be conveniently arranged to form an expression cassette comprising a 5'-fragment (the promoter region of the SSU gene), a 3'-fragment and a linker region connecting the two fragments. The fusion points between the 5'-fragment and the linker region and between the 3'-fragment and the linker region are preferably modified to create restriction sites which permit the antisense DNA of the present invention to be substituted for the linker so as to yield "chimeric" genes containing the complete proximal 5'- and 3'-regions of the SSU gene but none of the SSU coding sequence Other plant promoter enhancer sequences which may be used in accordance with the present invention have been described in the following references: Coruzzi, et al., "Tissue Specific and Light Regulated Expression of a pea nuclear gene encoding the small subunit of ribulose-1,5-bisphosphate carboxylate", EMBO Journal, vol. 5, no. 8, pp. 1671–1679 (1984) Apel, et al., "The Plastid Membranes of Barley (Hordeum Vulgare)", Eur. J. Became. 85:581–588 (1978); Stiekema, et al., "Phytochrome control of the Expression of Two Nuclear Genes Encoding Chloroplast Proteins in Lemna Gibba L. G-3", (1983), Plant Physiol. 72:717–724; Thompson, et al., "Phytochrome control of RNA Levels in developing pea dn mung bean leaves", (1983), Planta 158:487–500; Jones, et al., "High Level Expression of introduced chiamaeric genes in regenerated transformed plants", (1985), The EMBO Journal, vol. 4, pp. 2411–2418; Stockhaus, et al., "Identification of Enhancer elements in the Upstream region of the Nuclear Photosynthtic Gene ST-LS1", (1989), The Plant Cell 1:805–814; Gurley, et al., 1986, *Mol. Cell Biol.* 6:559–565; Landsmann, et al., "Organ regulated Expression of the *Parasponia andersonii* haemoglobin gene in Transgenic tobacco Plants", Mol. Gen. Genet. vol. 214, pp. 68–73 (1988); Bevan, et al., "Tissue and Cell specific activity of a phenylaline ammonialylase promoter EMBO J. 8:1899–1906 (1989); Benfey, et al., "The CaMV 35S Enhancer Contains At Least Two Domains Which Can Confer Different Developmental and Tissue Specific Expression Patterns" EMBO J. 8: 2195–2202 (1989); Ranu, Plant Promoter, U.S. Patent Application No. 60/203021, each hereby incorporated by reference.

Certain bacterial promoters have been observed to be expressed in plants, including the *Rhizobium meliloti* FIXD gene promoter (Puhler, et al., U.S. Pat. No. 4,782,022) and the nopaline synthase promoter (Ha, et al., "Cis-scting regulatory elements controlling temporal and organ specific activity of nopaline synthase promoter", Nucl. Acids Res., vol. 17, pp. 215–224, (1989); An, et al., "Organ Specific and Developemental Regulation of the Nopaline Synthase Promoter in Transgenic Tobacco Plants.", Plant Physiology 88:547–552 (1988)). Several promoter sequences, termed the rol A, B and C promoters, have been identified in *Agrobacterium rhizogenes* (Schmulling, et al., "Promoters of the rolA, B and C Genes of *Agrobactrium Rhizogenes* are differentially regulated in transgenic plants", (1989), Plant Cell 1, pp. 665–670; Sugaya, et al., "Cell Specific Expression of the RolC Gene of the TL-DNA of Ri Plasmid in Transgenic Tobacco Plants", (1989), Plant Cell Physiol. 30:649–654).

To test the activity of a promoter, *E. coli* β-glucuronidase (GUS) coding sequence or a mutant Arabidopsis EPSP synthase gene which encodes an enzyme tolerant of glyphosate herbicides may be used as a reporter gene. Transformed plant cells or plants containing the GUS gene operably linked to the promoter being tested are assayed using a histological staining procedure to determine GUS activity in the transformed cells.

The present invention provides antisense oligonucleotides and polynucleotides complementary to the gene, genes, or gene fragments encoding ACC synthase in geranium plants. Such antisense oligonucleotides, should be at least about six nucleotides in length to provide minimal specificity of hybridization, and may be complementary to one strand of DNA or to mRNA encoding ACC synthase (or to a portion thereof), or to flanking sequences in genomic DNA which are involved in regulating ACC synthase gene expression. The antisense oligonucleotide may be as large as about 100 nucleotides, an may extend in length up to and beyond the full coding sequence for which it is antisense. The oligonucleotides can be DNA or RNA or chimeric mixtures or derivatives or modified versions thereof, single-stranded or double-stranded.

The action of the antisense nucleotide may result in specific alteration, primarily inhibition, of ACC synthase gene expression in cells. For a general discussion of antisense, see: Alberts, B., et al., Molecular Biology of the Cell, 2nd Ed., Garland Publishing, Inc., New York, N.Y. (1989), pp. 195–196).

The antisense oligonucleotide may be complementary to any portion of the ACC synthase encoding sequence. In one embodiment, the antisense oligonucleotide may be between about 6 and 100 nucleotides, and may be complementary to the initiation ATG codon and an upstream, non-coding translation initiation site of the ACC synthase sequence. For example, antisense nucleotides complementary primarily for non-coding sequence, are known to be effective inhibitors of the expression of genes encoding transcription factors (Brach, M. A., "The Mitogenic Response to Tumor Necrosis Factor Alpha Requires c-Jun/AP-1", Molec. Cell. Biol. vol. 13, no. 7, pp. 4284–4290 (1993)).

Preferred antisense oligonucleotides are complementary to a portion of the mRNA encoding ACC synthase. For instance, it is expected that by introducing a full length cDNA clone gene in an antisense orientation, successful alteration of gene expression will be most probable. Naturally, introduction of partial sequences, targeting to specific regions of the gene, and the like can be effective as well. An example of a preferred antisense oligonucleotide is a 50 mer which is antisense to 50 nucleotides in the 5'-half of an RNA transcript of an ACC-encoding cDNA, more preferably any stretch of 50 nucleotides in the first 500 nucleotides of the 5'-part of the RNA transcript. For example, the antisense oligonucleotide can be antisense to nucleotides 1–50, 2–51, 3–52, 4–53,5–54, etc., of the RNA transcript. Alternatively, the antisense oligonucleotide can be shorter, for example a 30-mer, and be antisense to any 30 nucleotide stretch of the RNA transcript, preferably in the first 500 5' nucleotides.

As is readily discernible by one of ordinary skill in the art, the minimal amount of homology required by the present invention is that sufficient to result in sufficient complementarity to provide recognition of the specific target RNA and inhibition or reduction of its translation or function while not affecting function of other mRNA molecules and the expression of other genes. While the antisense oligonucleotides of the invention comprise sequences complementary to at least a portion of an RNA transcript of ACC synthase, absolute complementarity, although preferred, may not be required. A sequence "complementary to at least a portion of" another sequence, as referred to herein, may have sufficient complementarity to be able to hybridize with that other sequences in vivo, perhaps forming a stable duplex. Naturally, the ability to hybridize may depend on both the degree of complementarity and the length of the antisense nucleic acid. Generally, the longer the hybridizing nucleic acid, the more base mismatches with the ACC synthase target sequence it may contain and still form a stable duplex. One skilled in the art can ascertain a tolerable degree of mismatch by use of standard procedures to determine the melting temperature of the hybridized complex as discussed above and other techniques.

The antisense RNA oligonucleotides generated intracellularly by transcription from exogenously introduced nucleic acid sequences. Thus, antisense RNA may be delivered to a cell by transformation or transfection or infection with a vector, such as a plasmid or a virus, into which is incorporated (a) DNA encoding the antisense RNA and operably linked thereto (b) the appropriate regulatory sequences, including a promoter, to express the antisense RNA in a target host cell (and whole plant). Within the cell the exogenous DNA or a portion thereof may be transcribed, producing an antisense RNA of the invention. Vectors can be plasmid, viral, or others known in the art which are used for replication and expression in plant cells. Expression of the sequence encoding the antisense RNA can be by any promoter known in the art to act in plant, preferably geranium, cells. Such promoters can be inducible or preferably are constitutive as described above. Such a vector, preferably a plasmid, becomes chromosomally integrated such that it can be transcribed to produce the desired antisense RNA. Such plasmid or viral vectors can be constructed by recombinant DNA technology methods that are standard in the art.

An oligonucleotide, between about 6 and about 100 bases in length and complementary to the target sequence of ACC synthase, as describe above may be prepared by chemical synthesis from mononucleotides or shorter oligonucleotides, or produced by recombinant means.

Basic procedures for constructing recombinant DNA and RNA molecules in accordance with the present invention are disclosed by Sambrook, J., Fritsch, E. F., and Maniatis, T., "Molecular Cloning: A Laboratory Manual", Cold Spring Harbor Laboratory Press (1989), which reference is herein incorporated by reference. Oligonucleotide molecules having a strand which encodes antisense RNA complementary to an ACC synthase sequence can be prepared using procedures which are well known to those of ordinary skill in the art. Details regarding such procedures are described in: Belagaje, R., et al., "Total Synthesis of a Tyrosine Suppressor Transfer RNA Gene J. Biol. Chem. 254: 5765–5780 (1979); Maniatis, T., et al., "In Vitro Synthesis and Molecular Cloning of Eukarotic Structural Genes", Molecular Mechanisms in the Control of Gene Expression, Nierlich, D. P. et al, Eds, Acad Press, NY, Vol. V, pp. 513–533 (1976); Wu, R., et al., "Synthetic Oligodcoxynucleotides for Analyses of DNA Structure and Function", Prog. Nucl. Acid Res. Molec. Biol. 21:101–141 (1978); Khorana, H. G., "Total Synthesis of a Gene", Science, vol. 203, pp. 614–625 (1979)). Automated synthesizers may be used for DNA synthesis (such as are commercially available from Biosearch, Applied Biosystems, etc.).

Techniques of nucleic acid hybridization are disclosed by Sambrook, J., Fritsch, E. F., and Maniatis, T., "Molecular Cloning: A Laboratory Manual", Cold Spring Harbor Laboratory Press (1989)), which references are herein incorporated by reference.

The transgenic plants of the present invention may be prepared by DNA transformation using any method of transformation known in the art. These methods include transformation by direct infection or co-cultivation of plants, plant tissue or cells with *Agrobacterium tumefaciens* (Horsch, et al., "A Simple and General Method for Tranferring Genes into Plants", Science, vol. 227 pp. 1229–1231, (1985); Marton, L., "Transformation of Tobacco Cells By Coculture with *Agrobacterium tumefaciens*", Cell Culture and Somatic Cell Genetic of Plants 1:514–521 (1984); Fry, et al., "Transformation of *Brassica Napus* with *Agrobacterium tumefaciens* based vectors", Plant Cell Reports, vol. 6, pp. 321–325 (1987)); direct gene transfer into protoplasts or protoplast uptake (Paszkowski, et al., "Direct Gene Transfer to Plants", EMBO Journal 12:2717–2722 (1984); Lorz, et al., "Gene Transfer to Cereal Cells Mediated by Protoplast Transformation", Mol. & Gen. Genet. vol. 199, pp. 178–182 (1985); electroporation Fromm, et al., Nature 319:719 (1986)); microprojectile or particle bombardment (Klein, et al., "Factors Influencing Gene Delivery in ZEA may Cells by High Velocity Micro Projectiles", Bio/Technology 6:559–563 (1988)); injection into protoplasts cultured cells and tissues (Reich et al., "Efficient Transformation of Alfalfa Protoplasts by the intranuclear Microinjection of TI Plasmids", Bio/Technology, 4:1001–1004 (1986)); or injection into meristematic tissues of seedlings and plants (De La Pena, et al., Transgenic Rye Plants Obtained by Injecting DNA into young Floral Tillers", Letters to Nature, Nature, Vol. 325, pp. 274–276, (1987); Graves, et al., "The transformation of *Zea Mays* seedlings with *Agrobacterium tumefaciens*", Plant Mol. Biol. vol. 7, pp. 43–50 (1986); Hooykaas-Van Slogteren, et al., "Expression of TI plasmid genes in monocotyledonous plants infected with *Agrobacterium tumefaciens*", Nature, vol. 311, pp. 763–764 (1984); Grimsley, et al., "Agrobacterium mediated delivery of infectious maize streak virus into maize plants", Nature, vol. 325, pp. 177–179 (1987); and Grimsley, et al., "Meristemic tissues of maize plants are most susceptible to agroinfection with maize streak virus", Bio-Technology vol. 6, 185–190, (1988);

The *Agrobacterium tumefaciens* strain 208 carrying the disarmed pMP90RK plasmid can be used to achieve transformation. Used for plant transformations, the vector plasmid may be introduced into the Agrobacterium by the triparental conjugation system (Ditta, G., et al., "Broad Host Range DNA Cloning System for Gram Negative Bacteria: Construction of a Gene Bank of Rhizobium Meliloti", Proc. Natl. Acad. Science, Vol. 77, No. 12, 7347–7451 (1980)) using the helper plasmid pRK2013. The vectors may be transferred to plant cells by the vir functions encoded by the disarmed pMP90RK Ti plasmid. The vector is opened at the pTiT37 right border sequence and the entire vector sequence is inserted into the host plant chromosome. The pMP90RK Ti plasmid is probably not transferred to the plant cell but remains in the Agrobacterium.

Normally, regeneration will be involved in obtaining a whole plant from the transformation process. The term "regeneration" as used herein, means growing a whole plant from a plant cell, a group of plant cells, a plant part or a plant piece (e.g. from a protoplast, callus, tissue part, or explant, etc.) Plant regeneration from cultured protoplasts is described in Evans, D. A., and Bravo, J. E., "Protoplast Isolation and Culture", Handbook of Plant Cell Cultures, 124–176 (1983); Davey, M. R., "Recent Developments in the culture and Regeneration of Plant Protoplasts", Protoplasts, pp.12–29, (1983); Dale, P. J., "Protoplast Culture and Plant Regeneration of Cereals and Other Recalcitrant Crops", Protoplasts, pp. 31–41, (1983); and Binding, H., "Regeneration of Plants", Plant Protoplasts, pp.21–73, (1985)).

Plant parts obtained from the regenerated plant in which expression of an ACC synthase gene has been altered, such as flowers, seeds, leaves, branches, fruit, and the like are included within the definition of "plant" as stated above, and are included within the scope of the invention. Progeny and variants and mutants of the regenerated plants are also included, especially if these parts comprise the introduced DNA sequences.

The present invention also provides ACC synthase proteins encoded for by the cDNA molecule described above.

A "functional derivative" of the ACC synthase protein may be a "fragment," "variant," "analog," or "chemical derivative" of ACC synthase, which retains at least a portion of the function of the ACC synthase which permits its utility in accordance with the present invention. Such function includes enzymatic activity or immunological crossreactivity with an antibody specific for ACC synthase. A fragment of the ACC synthase protein refers to any subset of the molecule, that is, a shorter peptide. A variant refers to a molecule substantially similar to either the entire protein or a fragment thereof. Variant peptides may be conveniently prepared by direct chemical synthesis using methods well-known in the art.

An "analog" of ACC synthase refers to a non-natural protein substantially similar to either the entire protein or a fragment thereof. A chemical derivative of ACC synthase contains additional chemical moieties not normally a part of the protein or peptide fragment thereof. Covalent modifications of an ACC synthase peptide are included within the scope of this invention. Such modifications may be introduced into the molecule by reacting targeted amino acid residues of the peptide with an organic derivatizing agent that is capable of reacting with selected side chains or terminal residues.

A protein or peptide according to the present invention may be produced by culturing a cell transformed with a DNA sequence of this invention, allowing the cell to synthesize the protein, and obtaining the protein from the culture medium if it is secreted, or if it is intracellular, obtaining it by extraction. In a preferred embodiment, the protein is produced in a cell free system, for example, as described by Ranu, R. S., et al., "Regulation of Protein Synthesis in Rabbit Reticulocyte Lysates: Preparation of Efficient Protein Synthesis Lysates and the Purification and Characterization of the Heme-Regulated Translational Inhibitory Protein Kinase", Methods in Enzymology, Vol. 60, (1979), pp. 459–484 and Ranu, R. S., et al., "In Vitro Translation of the Full-Length RNA Transcript of Figwort Mosaic Virus (Caulimovirus)", Gene Expression, Volume 5, (1996), pp. 143–153.

To produce an isolated, purified protein or peptide, the in vitro translation product or the cell or tissue extract from transformed plant cells or plant parts is subjected to conventional biochemical purification methods, including but not limited to affinity chromatography using an antibody specific for an epitope of the protein.

Having now generally described the invention, the same will be more readily understood through reference to the following examples which are provided by way of illustration, and are not intended to be limiting of the present invention, unless specified.

EXAMPLES

Plant Material

*Pelargonium hortorum* cv *sincerity* (geranium) plants grown and maintained in a greenhouse were used to clone the cDNA corresponding to ACC synthase genes. Flower tissue in the form of senescing flower petals (from different stages) were collected in liquid nitrogen and used immediately or stored at −70° C. until use.

Messenger RNA (mRNA) Isolation

The quality of the mRNA largely determines the quality of cDNA library generated subsequently for cDNA cloning of ACC synthase gene. The term "quality of the mRNA" means the presence of desired mRNA species, especially those mRNA molecules that are present in cells in relatively low abundance (either because of the number of gene copies, the rate of transcription or the stability of the mRNA). The most widely used method for preparation of RNA utilizes extraction with 4 M guanidine thiocyanate of total RNA (Chomczynski, P., et al., "Single-Step Method of RNA Isolation by Acid Guanidinium Thiocyanate-Phenol-Chloroform Extraction", Analytical Biochemistry, vol. 162, pp. 156–159 (1987)). When this method was tried by the present inventor, the quality of RNA obtained was inadequate and did not permit the generation of a useable, high quality cDNA library (containing cDNA inserts corresponding to the least abundant mRNAs). Thus, when cDNA libraries prepared using the conventional method were screened for the presence of cDNA inserts encoding ACC synthase, the clones identified contained only partial genes or, mostly frequently, false positives. This problem alone made the process of isolating the ACC synthase genes of this invention extremely difficult and challenging. This conclusion was also suggested from the results of expression screening of such libraries with antibodies specific for the ACC synthase protein. In sum, the prior art RNA isolation technique at best invited experiments to try to find the full length genes, but provided no reasonable expectation of success. Problems posed by the poor quality of the total RNA prepared using conventional methods led the present inventor to look for alternative means for obtaining RNA of sufficiently high quality to be useful for the purposes of this invention, namely preparation of a cDNA library having a high probability of including a full length DNA sequences corresponding to low-abundance mRNAs, in particular full-length ACC synthase coding sequences.

Preparation of RNA

The preferred method discovered by the present inventor was based on the precipitation of RNA from a tissue extract using 2-butoxyethanol (Manning, K., "Isolation of Nucleic Acids from Plants by Differential Solvent Precipitation", Analytical Biochemistry (1991), pp. 45–50) with modifications. This method is referred to herein as "a 2-butoxyethanol precipitation technique." This technique was originally developed for RNA isolation, and by adapting it for mRNA isolation, the extraordinary results of this invention were achieved. Generally, in order to achieve the required RNA precipitation, a co-precipitation critical mass of RNA must be present in the preparation. The relative low proportion of RNA in relation to the total extracted material required the recognition by the present inventor that the standard amount of tissue extract used in RNA preparation, about 1 gram or less, would be insufficient for certain types of plants such as geranium (discussed more fully below). The success described herein was ultimately attained by using an unusually large amount of tissue. For the effort with geranium, this was about 3–5 grams. While, in hindsight, this may seem like a simple problem and solution, in fact, this problem does not appear to have been considered by others, and, therefore, the novel method is not an obvious modification of the older technique.

This problem in part stems from the fact that the desired precipitation is "non-linear," meaning that no simple linear relationship exists between the mass of RNA and the amount of precipitation. Rather, the process is a threshold phenomenon, and unless that critical mass is present, precipitation will not occur. For these reasons, the prior art technique would appear on its face to be inapplicable for obtaining a high quality mRNA preparation from woody plants such as geranium. Surpassing such a critical amount of RNA, that is, an amount at which precipitation occurs, permitted the method, as modified, to demonstrate its full utility. Hence, the present inventor achieved an unexpected and extraordinary result, in spite of the fact that the technology underlying the modifications introduced to earlier methods had been available. Those of ordinary skill in the art may have appreciated (although this is not evident) that a key impediment was in the obtaining of high quality mRNA to generate a fully representative cDNA library. Furthermore, a long felt need in the art for such a library had not been satisfied. Nevertheless, substantial attempts in the prior art failed because practitioners did not understand the true nature of the reasons for failure of this type of technique.

The present inventor's discovery of a means to here achieve the co-precipitation critical mass of RNA is particularly important to the class of plants which have a low proportion of RNA in their tissue, such as less than only $\frac{1}{10,000}$th of the total tissue usually obtained. It is also particularly important for woody plants such as geranium, for which the present invention is particularly useful. These groups of plants comprises plant species that have a low proportion of RNA in their tissue relative to non-nucleic acid material. This is in contrast to other plants which have a higher proportion of RNA and are amenable to the preparation of high quality mRNA (and cDNA corresponding thereto) by the traditional approaches of the prior art. While this "low RNA" group of plants is known to include at least Pelargonium species and Rosa (rose) species, it is clear that other plants also fall in this category, as would be evident to those skilled in the art. This group of plants is characterized in one manner as being woody (that is, they contain large amounts of fiberous material) and therefore having a low relative abundance of RNA, or conversely, as a high relative proportion of non-nucleic acid material. Thus, in this category of low RNA plants, it would be necessary to use a "large" amount of tissue, namely, an amount which (depending upon the particular plant or technique) is sufficient to yield a co-precipitant critical mass of total RNA in the process. For Pelargonium, Rosa, and the like, a co-precipitant critical mass of RNA is about 200 µg for successful implementation of the 2-butoxyethanol precipitation technique described herein. (Other RNA isolation techniques or plants may, of course, each have their own critical mass, that is, the presence of enough total RNA for precipitation to actually occur.) Thus, for the present technique and plants, about 3–5 grams of flower tissue was used initially. This may represent a minimum amount for some plants. Naturally more would also work.

The flower tissue was ground into a powder using a pestle and mortar precooled by liquid nitrogen. The resulting material was then ground with 12–20 ml of extraction buffer (0.2M boric acid/Tris-HCl and 10 mM EDTA (pH 7.6)), followed by addition of 0.24–0.4 ml of 25% sodium dodecyl sulfate (SDS) and 0.24–0.4 ml of 2-mercaptoethanol (2-ME).

The mixture was brought to room temperature and extracted with an equal volume of extraction buffer, saturated phenol/chloroform mixture. The mixture was centrifuged at 20,000×g at room temperature. The upper aqueous phase was collected and kept in a fresh tube. The interphase and lower organic phase were re-extracted with an equal volume of extraction buffer containing SDS and 2-ME. After centrifugation at 20,000×g, the second aqueous phase was removed and combined with the first aqueous phase. The pooled aqueous phase was diluted with 2.5 volume of water and a quantity of 1M sodium acetate (pH 4.5) sufficient to make the final concentration 80 mM.

This was followed by addition of 0.4 volumes of 2-butoxyethanol (2-BE). After 30 minutes on ice, the mixture was centrifuged at 20,000×g for 10 minutes at 0° C. The clear supernatant was collected. Additional 2-BE was added to bring the total to one volume. After 30 minutes on ice, the nucleic acid-containing pellet was collected by centrifugation at 20,000×g for 10 minutes at 0° C. The pellet was washed first with a 1:1 (v/v) mixture of extraction buffer and 2-BE, followed by 70% ethanol containing 0.1M potassium acetate (pH 6.0), and finally with 100% ethanol. The pellet was then air dried.

The nucleic acid pellet was dissolved in water to a concentration of about 1 mg/ml and sufficient 12M LiCl was added to bring the LiCl concentration to 3M. After one hour on ice, an RNA precipitate was collected by centrifugation at 12,000×g for 10 minutes at 0° C. The pellet was washed twice with 3M LiCl and once with 70% ethanol and was finally air dried. RNA was dissolved 0.2–0.5 ml of 10 mM Tris-HCl, 1 mM EDTA (pH 8.0) (TE buffer).

Isolation of mRNA

PolyA$^+$mRNA was isolated by binding to Dynabeads-oligo(dT)25 (Dynal, Inc., Lake Success, N.Y.). The oligo (dT)25 is a preferred binding partner, in addition others are known in the art, the key function being merely the ability to selectively attach to the mRNA. For this binding partner, the protocol provided by the manufacturer was used. PolyA$^+$ RNA was bound to Dynabeads in the presence of 1×binding buffer for 30 minutes. The Dynabeads serve as one of the many possible solid phase supports or carriers. This served to immobilize the mRNA. The beads were washed three times with washing buffer containing lithium dodecyl sulfate (LiDS) and once with wash buffer alone. mRNA was eluted from the beads with 50 µl of TE buffer.

The composition of the buffers was as follows:

(a) 1×Binding Buffer: 10 mM Tris-HCl (pH 7.5), 0.5M LiCl, 1 mM EDTA, 0.5% LiDS;

(b) Washing Buffer with LiDS: 10 mM Tris-HCl, 0.15M LiCl, 1 mM EDTA, 0.1% LiDS

Synthesis of cDNA

Figure 2:
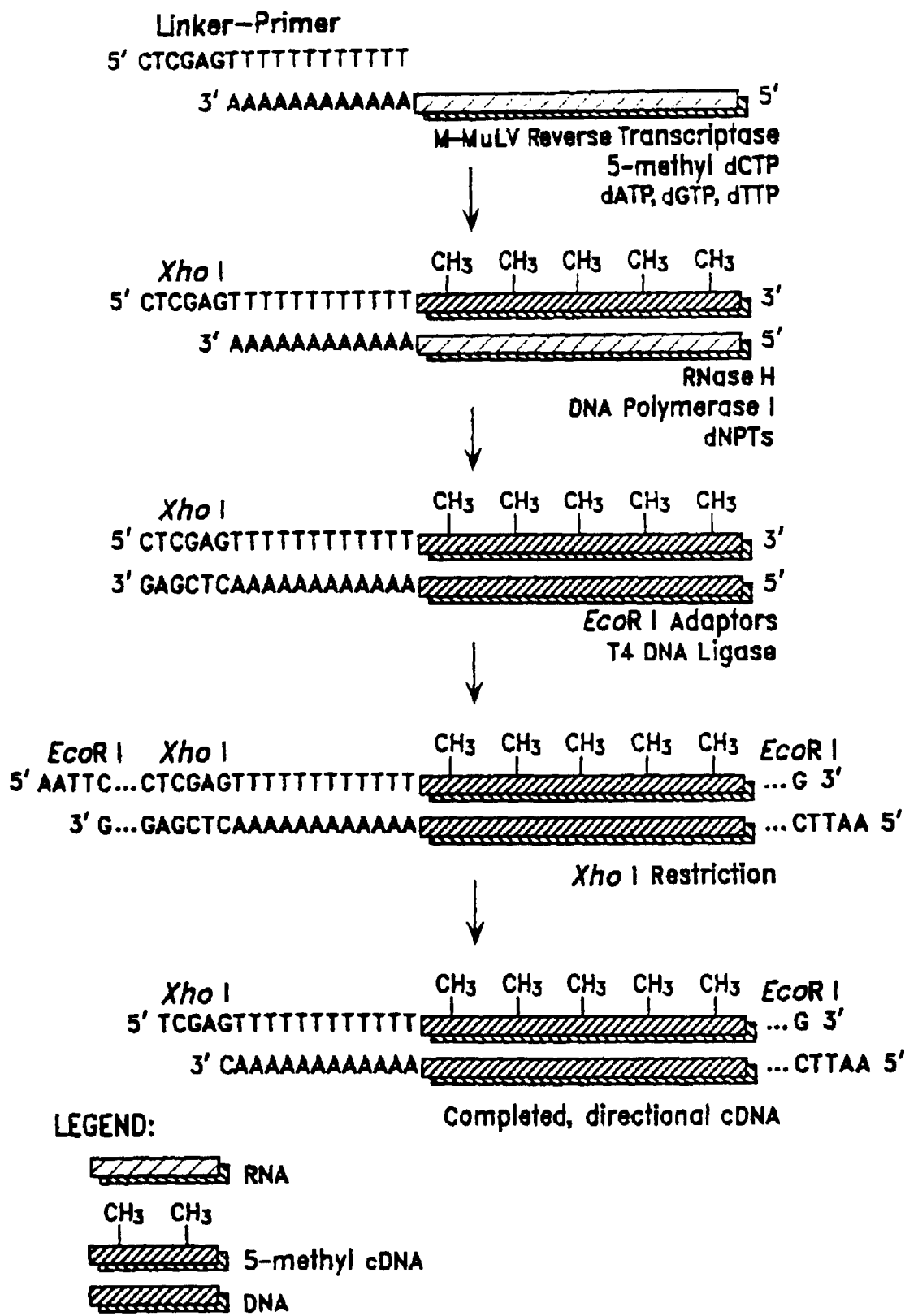
FIG. 2 is a diagram showing the details of steps of cDNA synthesis from mRNA

The mRNA preparation (5 µg) isolated as above was used to synthesize cDNA using the ZAP Express® cDNA synthesis system from Stratagene (La Jolla, Calif.). The details of the steps of synthesis are presented in FIG. 2. The first strand synthesis was carried out with murine-Moloney leukemia virus reverse transcriptase (M-MuLV-RT) in the presence of mRNA, a primer containing a 50 base long oligonucleotide

with an XhoI restriction recognition site (shown underscored). This allows the finished cDNA to be inserted into the ZAP Express® Vector in the sense orientation (EcoRI-XhoI) with respect to the LacZ promoter. The poly (dT) region binds to the poly(A) tail of mRNA template and the reverse transcriptase starts the synthesis of first strand. The nucleotide mixture for the synthesis of first strand contained DATP, dGTP, dTTP, and 5-methyldCTP. The first strand has methyl groups on each cytosine base which protects cDNA from restriction enzymes used in subsequent cloning steps.

RNase H nicks the RNA bound to the first strand cDNA to produce multiple fragments which serve as primers for DNA polymerase I (PolI). PolI nick-translates the RNA fragments into second strand of cDNA. The cDNA ends are blunted in the presence of Klenow fragment and dNTPs. The EcoRI adaptors as shown below

are ligated to the blunt ends. The XhoI digestion of cDNA releases the EcoRI adaptor and residual linker-primer from 3'-end of the cDNA. The cDNA is size fractionated on Sephacryl-S400® and then ligated to the ZAP Express Vector® arms.

Only cDNA of 1.5 kb pairs was used to ligate into ZAP Express Vector® and then packaged into bacteriophages using Gigapack® III Gold Packaging extract protocol from Stratagene. The unamplified cDNA library generated in this way was used for subsequent screening for ACC synthase genes.

Development of a Polymerase Chain Reaction (PCR) Probe for the Screening of ACC Synthase Genes The first strand of cDNA synthesis was carried out with 2 µg of mRNA using the ready-to-go T-Primed First-Strand synthesis protocol obtained from Pharmacia Biotechnology (Piscataway, N.J.). The first strand cDNA product was then used to develop a PCR probe. PCR amplification (Mullis, K. B., et al., "Specific Synthesis of DNA in Vitro via a Polymerase-Catalyzed Chain Reaction", Methods in Enzymology, (1987), pp. 335–350) was performed in a Techne PHC-2 Thermocycler (Techne, Princeton, N.J.).

The following PCR primers were used:

Primer I:

This is alternately designated as:

Primer II:

This is alternately designated as:

The PCR reaction (50 µl) contained 5 mM Tris-HCl (pH 8.3); 3 mM MgCl$_2$, 50 mM KCl, 50 pmol of primer I: 3 µl of synthesized first strand cDNA, 200 mM each of the four dNTPs and 25 units of—(DELTA) Taq DNA polymerase (Amersham Life Sciences, Inc., Arlington Heights, Ill.). Reaction samples were overlaid with 20 µl of mineral oil. After an initial denaturation at 95° C. for 4 minutes, samples were subjected to two cycles in which conditions were 94° C. for one minute for denaturation, 60° C. for two minutes for annealing; and 72° C. for one minute for extension. It was followed by 30 cycles at 94° C. for 30 seconds; 60° C. for one minute; and 72° C. for 45 seconds. The last cycle was at 72° C. for 5 minutes.

On analysis by agarose gel electrophoresis, the amplified DNA showed a DNA band of about 360 bp. The band was localized in the gel under a UV lamp and excised. DNA from the gel was purified by using Spin-Bind Recovery system from FMC BioProducts (Rockland, Me.). The DNA was then cloned using the protocol provided by manufacturer into a TA Cloning Vector called pCRII (Invitrogen, San Diego, Calif.) and then sequenced.

One of these clones was identified as PHSacc25. The sequence of this clone differed from the other clones.

DNA Sequencing of Clones

The dideoxy chain termination method (Sanger, F., et al., "DNA sequencing with chain-terminating inhibitors", Proc. Natl. Acad. Sci., (1977), pp. 5463–5467) was used to sequence the ACC synthase cDNA clones. This method employed the DELTA Taq DNA polymerase protocol developed in the present inventor's laboratory (Ranu R. S., "DNA Sequencing With Taq-DNA Polymerase", Biotechniques, (1995), pp. 390–393) or Thermo Sequenase® (Amersham, Inc.).

DEPOSIT

The following illustrative plasmids encoding geranium ACC synthase were deposited at the American Type Culture Collection, Rockville, Md., prior to the filing date of this application for patent under the requirements of the Budapest Treaty. These deposits were granted the following accession numbers and are hereby incorporated by reference:

1. pPHSacc25 cDNA clone comprising SEQ ID NO:1— accessions number ATCC PTA-3726.

The discussion included in this United States patent application is intended to serve as a basic description of the invention. The reader should be aware that the specific discussion may not explicitly describe all the embodiments of the invention that are possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in functionally-oriented terminology, each aspect of the function can be accomplished by a device, subroutine, or program. Apparatus claims may not only be included for the devices described, but also method or process claims may be included to address the functions the inventions and each element performs. Neither the description nor the terminology is intended to limit the scope of the claims.

Further, each of the various elements of the invention and claims may also be achieved in a variety of manners. This disclosure should be understood to encompass each such variation, be it a variation of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered encompassed in the description of each element or action. Such terms can be substituted where desired to make explicit the implicitly broad coverage to which this invention is entitled. As but one example, it should be understood that all actions may be expressed as a means for taking that action or as an element that causes that action. Similarly, each physical element disclosed should be understood to encompass a disclosure of the action that physical element facilitates. Regarding this last aspect, as but one example, the disclosure of a "clone" should be understood to encompass disclosure of the act of "cloning"—whether explicitly discussed or not—and, conversely, were there only disclosure of the act of "cloning", such a disclosure should be understood to encompass disclosure of a "cloning" and even a means for "cloning". Such changes and alternative terms are to be understood to be explicitly included in the description.

Additionally, various combinations and permutations of all elements of applications can be created and presented. All can be done to optimize the design or performance in specific applications.

Any acts of law, statutes, regulations, or rules mentioned in this application for patent; or patent, publications, or other references mentioned in this application for patent are hereby incorporated by reference herein. Specifically, U.S. Provisional Patent Application No. 60/239,782, filed on Oct. 12, 2000; U.S. patent application Ser. No. 08/724,194, filed on Oct. 1, 1996, now issued as U.S. Pat. No. 5,824,875; PCT/US97/17644, filed Sep. 30, 1997; PCT/US01/15023, filed May 9, 2001; U.S. patent application Ser. No. 09/171, 482, now issues as U.S. Pat. No. 6,184,449; and U.S. patent application Ser. No. 09/776, are each hereby incorporated by reference in their entirety herein.

In addition, as to each term used it should be understood that unless its utilization in this application is inconsistent with such interpretation, common dictionary definitions should be understood as incorporated by reference for each term and all definitions, alternative terms, and synonyms such as contained in the Random House Webster's Unabridged Dictionary, second edition are hereby incorporated by reference. However, as to each of the above, to the extent that such information or statements incorporated by reference might be considered inconsistent with the patenting of this/these invention(s) such statements are expressly not to be considered as made by the applicant(s).

Thus, the applicant(s) should be understood to have support to claim at least: i) the partial gene sequence derived from pPHacc25 as described herein, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the application enhanced by the various systems or components disclosed, vii) the resulting products produced by such systems or components, ix) methods and apparatuses substantially as described hereinbefore and with reference to any of the accompanying examples, and x) the various combinations and permutations of each of the elements disclosed.

In addition, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible in countries such as Australia and the like.

The claims set forth in this specification by are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

What is claimed is:
1. An isolated DNA molecule consisting of SEQ ID NO: 1.

* * * * *